(12) United States Patent
Ferguson, II et al.

(10) Patent No.: US 7,519,417 B2
(45) Date of Patent: Apr. 14, 2009

(54) QUANTITATIVE FETAL HEART RATE AND CARDIOTOCOGRAPHIC MONITORING SYSTEM AND RELATED METHOD THEREOF

(75) Inventors: James E. Ferguson, II, Lexington, KY (US); M. Pamela Griffin, Charlottesville, VA (US); J. Randall Moorman, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 504 days.

(21) Appl. No.: 10/545,257

(22) PCT Filed: Feb. 12, 2004

(86) PCT No.: PCT/US2004/004113

§ 371 (c)(1),
(2), (4) Date: Aug. 10, 2005

(87) PCT Pub. No.: WO2004/072822

PCT Pub. Date: Aug. 26, 2004

(65) Prior Publication Data

US 2006/0074329 A1      Apr. 6, 2006

Related U.S. Application Data

(60) Provisional application No. 60/493,411, filed on Aug. 7, 2003, provisional application No. 60/446,865, filed on Feb. 12, 2003.

(51) Int. Cl.
 *A61B 5/04*         (2006.01)

(52) U.S. Cl. ...................................................... 600/511
(58) Field of Classification Search ................. 600/453, 600/509, 511, 591
See application file for complete search history.

(56) References Cited

U.S. PATENT DOCUMENTS

| | | | | |
|---|---|---|---|---|
| 3,599,628 | A | * | 8/1971 | Abbenante et al. ........... 600/511 |
| 3,989,034 | A | * | 11/1976 | Hojaiban ..................... 600/511 |
| 4,537,200 | A | * | 8/1985 | Widrow ....................... 600/509 |
| 5,442,940 | A | | 8/1995 | Secker |
| 5,596,993 | A | | 1/1997 | Oriol |
| 5,954,663 | A | * | 9/1999 | Gat .............................. 600/511 |
| 5,957,855 | A | | 9/1999 | Oriol |
| 6,216,032 | B1 | | 4/2001 | Griffin |
| 6,231,524 | B1 | | 5/2001 | Wallace |
| 6,254,537 | B1 | | 7/2001 | Nguyen |
| 6,330,469 | B1 | | 12/2001 | Griffin |
| 6,804,551 | B2 | | 10/2004 | Griffin |
| 6,856,831 | B2 | | 2/2005 | Griffin |

* cited by examiner

*Primary Examiner*—George Manuel
(74) *Attorney, Agent, or Firm*—Robert J. Decker

(57) ABSTRACT

A method, system, and computer program product are provide for, among other things, quantitative analysis of heart rate characteristics from fetal heart rate and cardiotocogram monitors that gives information about the well-being of the fetus and the risk of poor fetal outcome. The method comprises (a) continuously measuring fetal heart rate and cardiotocographic characteristics and (b) identifying at least one characteristic abnormality in the heart rate characteristics that is associated with fetal distress. Benefits are appreciated by the fetus and the mother and during the antepartum and intrapartum periods.

29 Claims, 11 Drawing Sheets

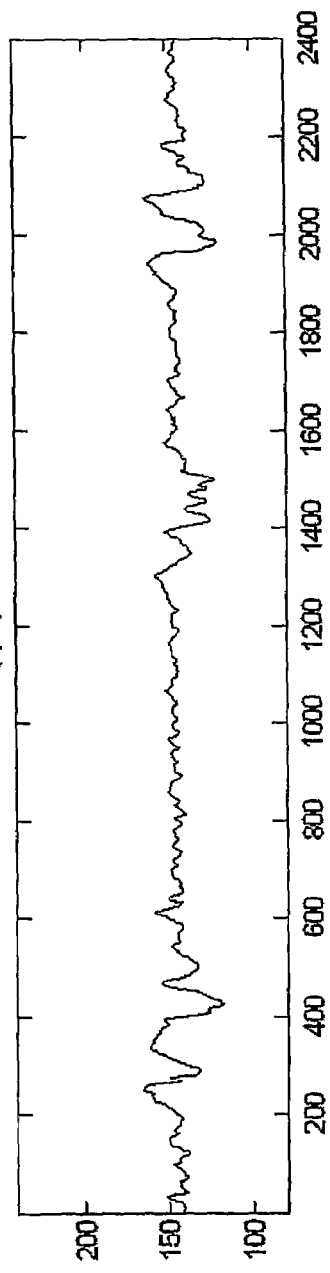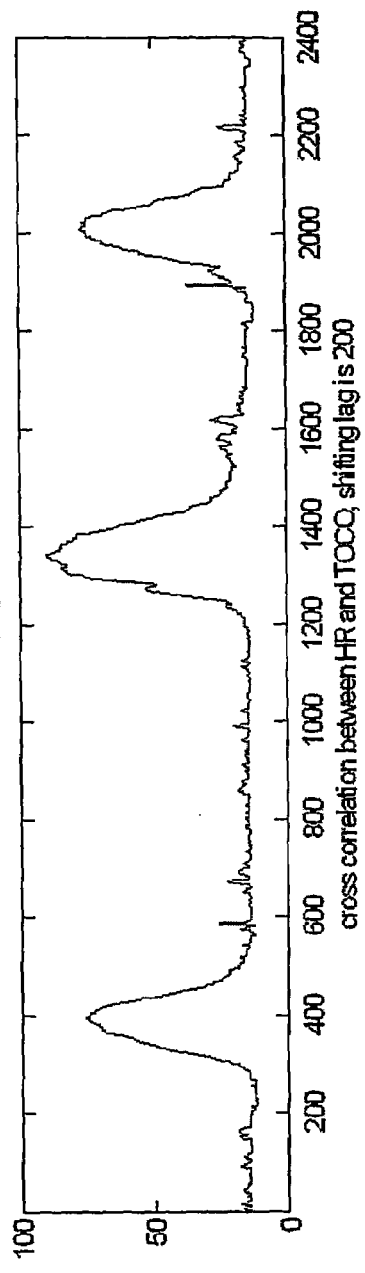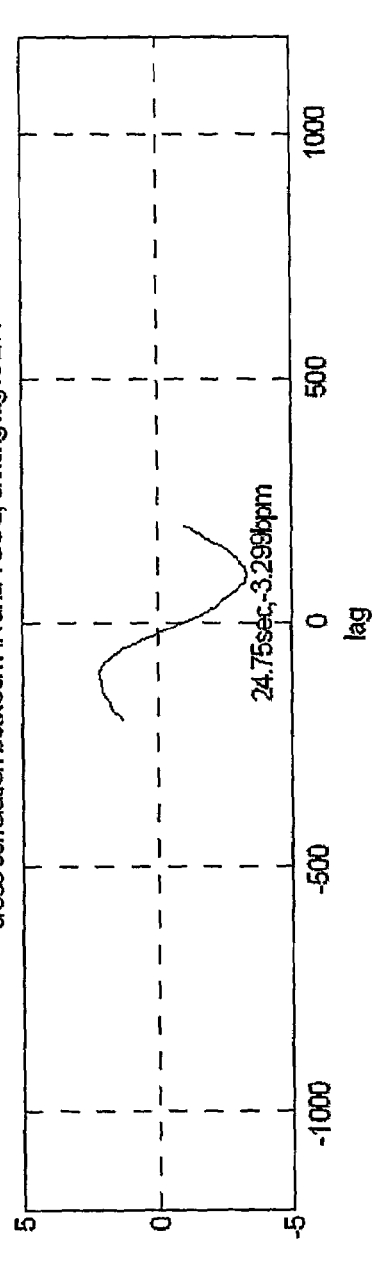
FIG. 1A
FIG. 1B
FIG. 1C

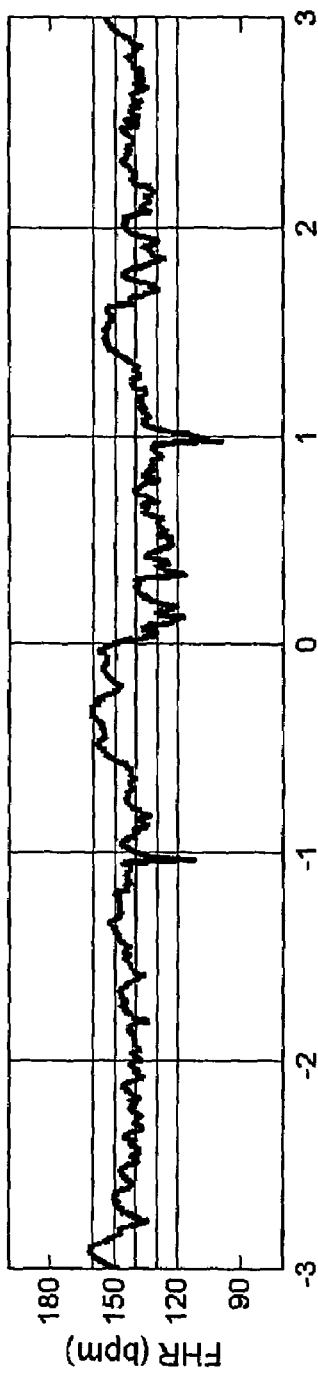
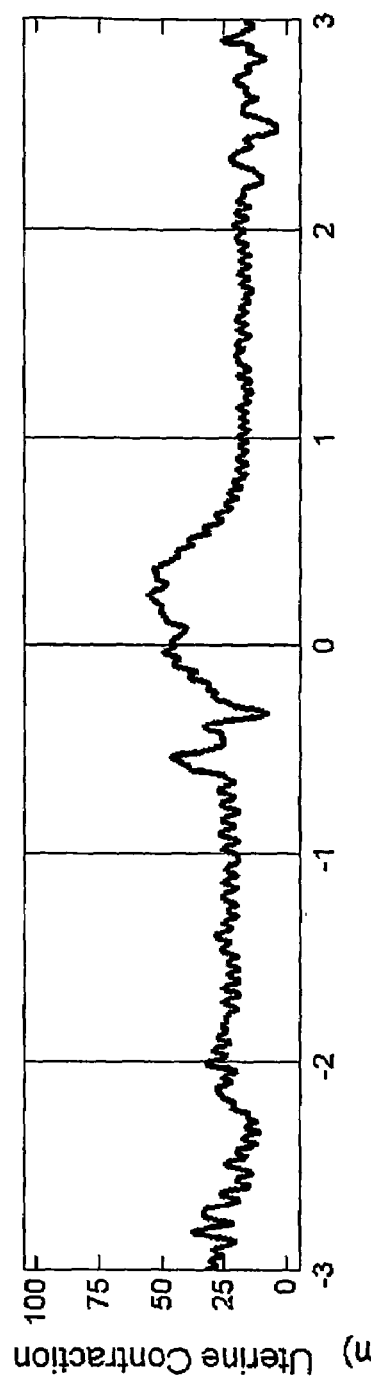
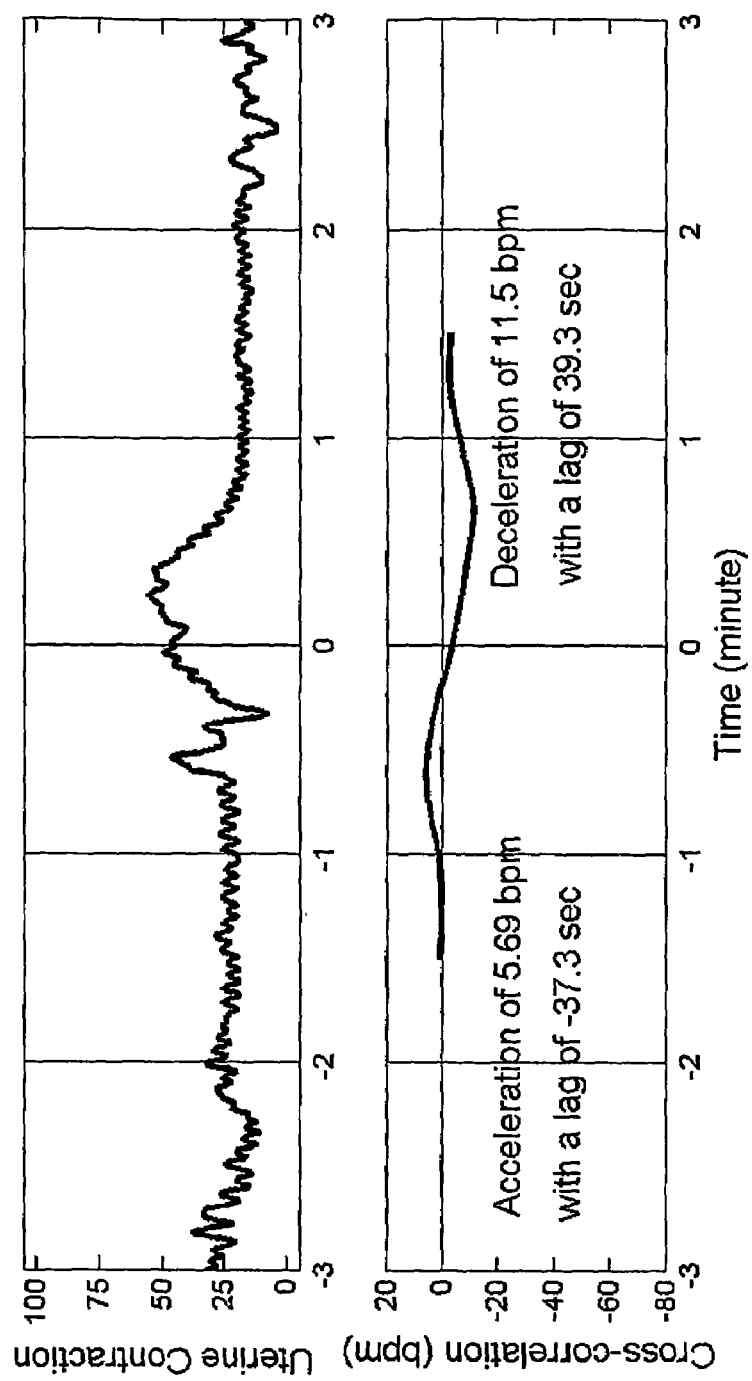
FIG. 5A
FIG. 5B
FIG. 5C

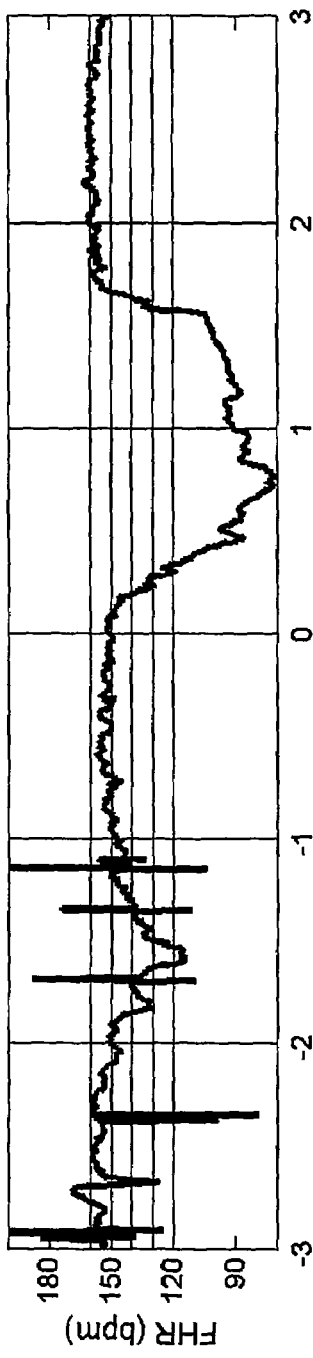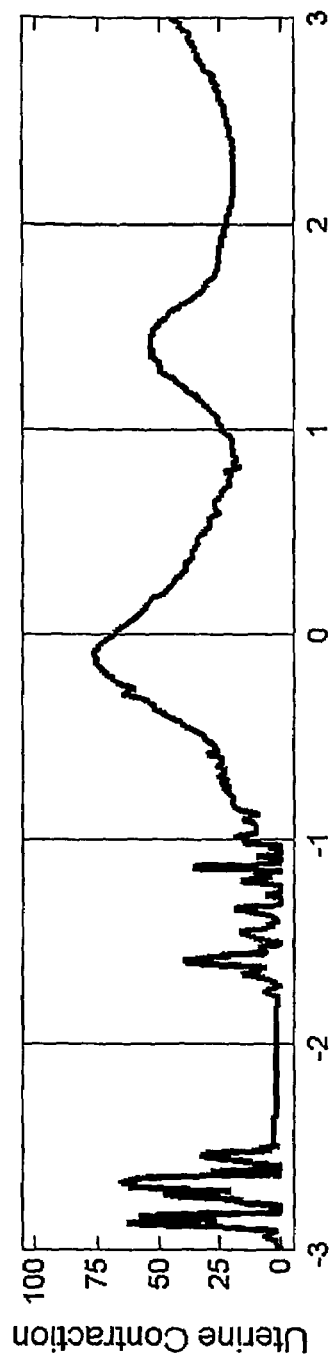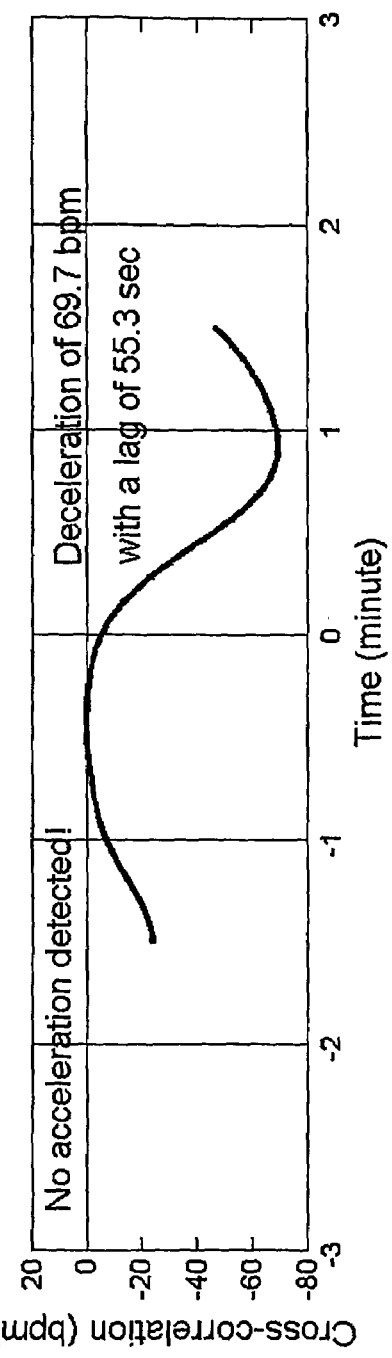
FIG. 6A
FIG. 6B
FIG. 6C

QUANTITATIVE FETAL HEART RATE AND CARDIOTOCOGRAPHIC MONITORING SYSTEM AND RELATED METHOD THEREOF

CROSS-REFERENCE TO RELATED APPLICATIONS

This application is a national stage filing of International Application No. PCT/US2004/004113, filed on Feb. 12, 2004, which claims benefit under 35 U.S.C. Section 119(e) of the earlier filing date of U.S. Provisional Application Ser. No. 60/446,865, filed Feb. 12, 2003, entitled "Quantitative Fetal Heart Rate Monitoring System and Related Method thereof" and U.S. Provisional Application Ser. No. 60/493,411, filed Aug. 7, 2003, entitled "Quantitative Fetal Heart Rate Monitoring System and Related Method thereof" which are hereby incorporated by reference herein in their entirety.

The present application is also related to: U.S. Pat. No. 6,216,032 B1 to Griffin et al., entitled "Method and Apparatus for the Early Detection of Subacute, Potentially, Catastrophic Illness;" U.S. Pat. No. 6,330,469 B1 to Griffin et al., entitled "Method and Apparatus for the Early Detection of Subacute, Potentially, Catastrophic Illness;" U.S. application Ser. No. 09/770,653, filed Jan. 29, 2001, now U.S. Pat. No. 6,856,831 issued Feb. 15, 2005, entitled "Method and Apparatus for the Early Detection of Subacute, Potentially, Catastrophic Illness;" and U.S. application Ser. No. 09/793,653 filed Feb. 27, 2001 now U.S. Pat. No. 6,804,551 issued Oct. 12, 2004, entitled "Method and Apparatus for the Early Detection of Subacute, Potentially, Catastrophic Illness," all of which are assigned to the present assignee and are hereby incorporated by reference herein in their entirety.

FIELD OF THE INVENTION

The present invention relates to a method, system, and computer program product for enhancing the clinical utility of fetal heart rate and cardiotocographic records by developing and implementing quantitative measures of abnormal features of fetal heart rate and cardiotocographic records.

BACKGROUND OF THE INVENTION

Continuous monitoring of the fetal heart rate is very commonly performed during active labor and for purposes of fetal stress testing. It has been recognized since the 1960's that a heart rate pattern showing reduced heart rate variability and transient decelerations signifies fetal distress, and observation of such characteristics often leads to surgical delivery of the fetus by Caesarian section. Improvements in fetal outcome due to this monitoring strategy, though, have been less than expected.

Electronic monitoring of the fetal heart rate (FHR) was developed the 1950s and became commercially available in the 1960s. See 1. Parer, J. T. and King, T. 2000, "Fetal Heart Rate Monitoring: Is it Salvageable?" *Am J Obstet. Gynecol.* 182:982-987, of which is hereby incorporated by reference herein. Physicians have learned to recognize qualitative features of FHR records that signify fetal distress. See Freeman, R. K., "Problems with Intrapartum Fetal Heart Rate Monitoring Interpretation and Patient Management," *Obstet.Gynecol.*, vol. 100, no. 4, pp. 813-826, October 2002. Classification of abnormal FHR patterns was developed in the 1960s and theories to correlate the fetal condition and FHR pattern were formulated. (See "Hon E. An Atlas of Fetal Heart Rate Patterns" *New Haven: Harty Press*; 1968. P. 1-31, of which is hereby incorporated by reference herein.) It was hoped that the introduction of FHR monitoring could serve as a screening test for asphyxia that is severe enough to cause neurologic damage or fetal death. It was thought that if an abnormal pattern was recognized that early obstetric intervention would avoid asphyxia-induced brain damage and death. See 1997 "Electronic Fetal Heart Rate Monitoring: Research Guidelines for Interpretation," National Institute of Child Health and Human Development Research Planning Workshop 1, *Am J Obstet. Gynecol.*, 177:1385-1390, of which is hereby incorporated by reference herein.

The American College of Obstetricians and Gynecologists recommends either intermittent auscultation or electronic FHR monitoring (EFM) as alternatives in low-risk pregnancies (See ACOG Technical Bulletin. Number 207. July, 1995). FHR and cardiotocogram (CTG) monitoring is widely utilized and in 1992 it was estimated that 74% of all pregnancies in the US were monitored electronically (See National Center for Health Statistics. Annual summary of birth, marriages, divorces, and deaths: United States, 1992. Month Vital Stat Rep 1993;41:28.)

While initial retrospective trials suggested EFM reduced stillbirth during labor (see Shenker, L., Post, R. C., and Seiler, J. S. 1975, "Routine Electronic Monitoring of Fetal Heart Rate and Uterine Activity During Labor," *Obstet Gynecol.*, 46:185-189 and Johnstone, F. D., Campbell, D. M., and Hughes, G. J., 1978, "Has Continuous Intrapartum Monitoring Made Any Impact On Fetal Outcome?" *Lancet* 1:1298-1300, of which are hereby incorporated by reference herein in their entirety), this clinical paradigm has been questioned. In a recent meta-analysis of 12 studies, involving nearly 60,000 patients a statistically significant decrease was associated with routine EFM for a 1-minute Apgar score of less than 4 and neonatal seizures, however the protective effect of EFM for a 1-minute score less than 4 was apparent only in the non-United States studies, and the protective effect for neonatal seizure was evident only in studies with high-quality scores. No significant differences were observed in 1-min Apgar scores less than 7, rate of admissions to neonatal intensive care units, and perinatal death. An increase associated with the use of EFM was observed in the rate of cesarean delivery and total operative delivery. Risk of cesarean delivery was greatest in low-risk pregnancies. See Thacker, S. B., Stroup, D. F. and Peterson, H. B., 1995, "Efficacy and Safety of Intrapartum Electronic Fetal Monitoring: an Update," *Obstet. Gynecol.*, 86:613-620, of which is hereby incorporated by reference herein.

One possible reason is that only qualitative interpretation of the heart rate characteristics is available, and different health care personnel might reach different conclusions about the same data. For example, the definition used in each trial for those FHR and CTG patterns necessitating obstetric intervention differed. There is, in addition, poor reliability of FHR and CTG interpretation. Studies assessing inter- and intra-observer agreement in interpretation of FHR tracings have found marked variability in interpretation in both normal and abnormal tracings. See Nielsen, P. V., Stigsby, B., Nickelsen, C. and Nim, J., 1988, "Computer Assessment of the Intrapartum Cardiotocogram. II. The Value of Compared with Visual Assessment," *Acta Obstet. Gynecol. Scand*, 67:461-464 and Cibils, L. A., 1996, "On Intrapartum Fetal Monitoring," *Am J Obstet. Gynecol.* 174:1382-1389, of which are hereby incorporated by reference herein in their entirety. Thus, inappropriate interpretation of FHR and CTG patterns signifying fetal jeopardy has led to inaccurate interpretation and inappropriate obstetric intervention.

A National Institutes of Health Research Planning Workshop published guidelines for interpreting FHR tracings (See 1997 "Electronic Fetal Heart Rate Monitoring: Research Guidelines for Interpretation," National Institute of Child Health and Human Development Research Planning Workshop 1, *Am J Obstet. Gynecol.*, 177:1385-1390), and commercial'systems to implement them are available.

Therefore, the optimal outcome of this approach is to reduce human error in using the guidelines, which have inherent limitations because the basis of the analysis is semi-quantitative. It is thus clear that the current methods of evaluating the FHR and CTG are less than optimal.

SUMMARY OF THE INVENTION

The present invention is a method, system, and computer program product are for, among other things, quantitative analysis of heart rate characteristics from fetal heart rate and/or CTG monitors that gives information about the well-being of the fetus and the risk of poor fetal outcome. The method comprises (a) continuously measuring fetal heart rate and/or cardiotocographic characteristics and (b) identifying at least one characteristic abnormality in the heart rate characteristics that is associated with fetal distress.

In an embodiment of the present invention, there is provided an apparatus for providing information about the well-being of the fetus and the risk of poor fetal outcome. The apparatus comprises: (a) a monitoring device that measures fetal heart rate and/or cardiotocographic characteristics and (b) microprocessor, identifying at least one characteristic abnormality in the heart rate and/or cardiotocographic characteristics that is associated with fetal distress.

In an embodiment, the at least one characteristic is identified from a normalized set of RR intervals, the times from one fetal heartbeat to the next or heart rates. The at least one characteristic is based on the identification of one or more of the following kinds of measures 1) the second and higher moments of the fetal heart rate; 2) the quantile or percentile values of the fetal heart rate; 3) the sample entropy of the fetal heart; 4) the sample asymmetry of the fetal heart rate; 5) Lomb periodogram of the fetal heart rate; and 6) cross-correlation of fetal heart rate and uterine pressure tracings.

In an embodiment of the present invention, the microprocessor may perform a variety of functions comprising, but not limited thereto, calculating: 1) the second and higher moments of the fetal heart rate; 2) the quantile or percentile values of the fetal heart rate; 3) the sample entropy of the fetal heart rate; 4) the sample asymmetry of the fetal heart rate; 5) Lomb periodogram of the fetal heart rate; and 6) cross-correlation of fetal heart rate and uterine pressure tracings.

Abnormal heart rate characteristics that are characteristic of fetal distress can be identified, for example, by comparing the above parameters of heart rate and/or cardiotocographic characteristics to threshold, or by combining multiple measurements in logistic regression models, neural networks, or other predictive mathematical instruments. Thresholds or mathematical modeling can be assigned, wherein ideally, these parameters will be based on the result of large group of, for example, non-distressed fetuses and distressed fetuses.

A purpose of the calculation discussed in this document is to identify decelerations of FHR that occur late relative to uterine contractions. A robust approach to investigating time-relationships between waveforms is cross-correlation. Conceptually, the operation is to slide one time series past the other; computing the sum of the products of the aligned terms. When similar structures of the two series are aligned, the sum will be large. Thus the expected findings of cross-correlation of the FHR and uterine pressure tracings when a deceleration is late are (1) a large and negative peak that (2) occurs after an appreciable shift of the series in time.

An aspect of an embodiment of the present invention includes a method for evaluating fetal well-being and predicting fetal outcome. The method comprising a) obtaining simultaneous recordings of fetal heart rate and maternal uterine pressure; and b) calculating one or more of: i) cross-correlation of the fetal heart rate and the uterine pressure, ii) Lomb periodogram of the fetal heart rate, iii) sample entropy of the fetal heart rate, iv) sample asymmetry of the fetal heart rate, and/or v) one or more of: second, third and fourth higher moments, or percentiles of interest of the fetal heart rate.

An aspect of an embodiment of the present invention includes an apparatus for evaluating fetal well-being and predicting fetal outcome. The apparatus comprising:

a) a monitoring device, which monitors the fetal heart rate and maternal uterine pressure; and b) a microprocessor, the microprocessor performing the steps of calculating one or more of: i) cross-correlation of the fetal heart rate and the uterine pressure, ii) Lomb periodogram of the fetal heart rate, iii) sample entropy of the fetal heart rate, iv) sample asymmetry of the fetal heart rate, and/or v) one or more of: second, third and fourth higher moments, or percentiles of interest of the fetal heart rate.

An aspect of an embodiment of the present invention includes a computer program product or the like comprising computer usable medium having computer logic for enabling at lease one processor or the like in a computer system or the like to evaluate fetal well-being and predicting fetal outcome based on a monitoring device, which monitors the fetal heart rate and maternal uterine pressure. The computer logic or the like comprising calculating one or more of: a) cross-correlation of the fetal heart rate and the uterine pressure, b) Lomb periodogram of the fetal heart rate, c) sample entropy of the fetal heart rate, d) sample asymmetry of the fetal heart rate, and/or e) one or more of second, third and fourth higher moments, or percentiles of interest of the fetal heart rate.

These and other objects, along with advantages and features of the invention disclosed herein, will be made more apparent from the description, drawings, and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which:

FIGS. 1(A)-(C) graphically illustrates a ten minute record representing a) FHR b) uterine contraction and c) cross-correlation representing the change in FHR relative to the uterine contraction, respectively.

uterine contraction and c) cross-correlation representing how the change in FHR relative to the uterine contraction, respectively.

FIGS. 5(A)-(C) graphically illustrates a six minute record representing a) FHR, b) uterine contraction and c) cross-correlation representing the change in FHR relative to the uterine contraction of a clinically normal record, respectively.

FIGS. 6(A)-(C) graphically illustrates a six minute record representing a) FHR, b) uterine contraction and c) cross-correlation representing the change in FHR relative to the uterine contraction of a clinically abnormal CTG record with a large late deceleration, respectively.

FIG. 7 is a graphical representation showing the frequency histograms of the deceleration, acceleration and related measures.

FIG. 8 is a graphical representation showing the frequency histograms of the band-specific variances from the Lomb periodogram analysis.

Figure 9:
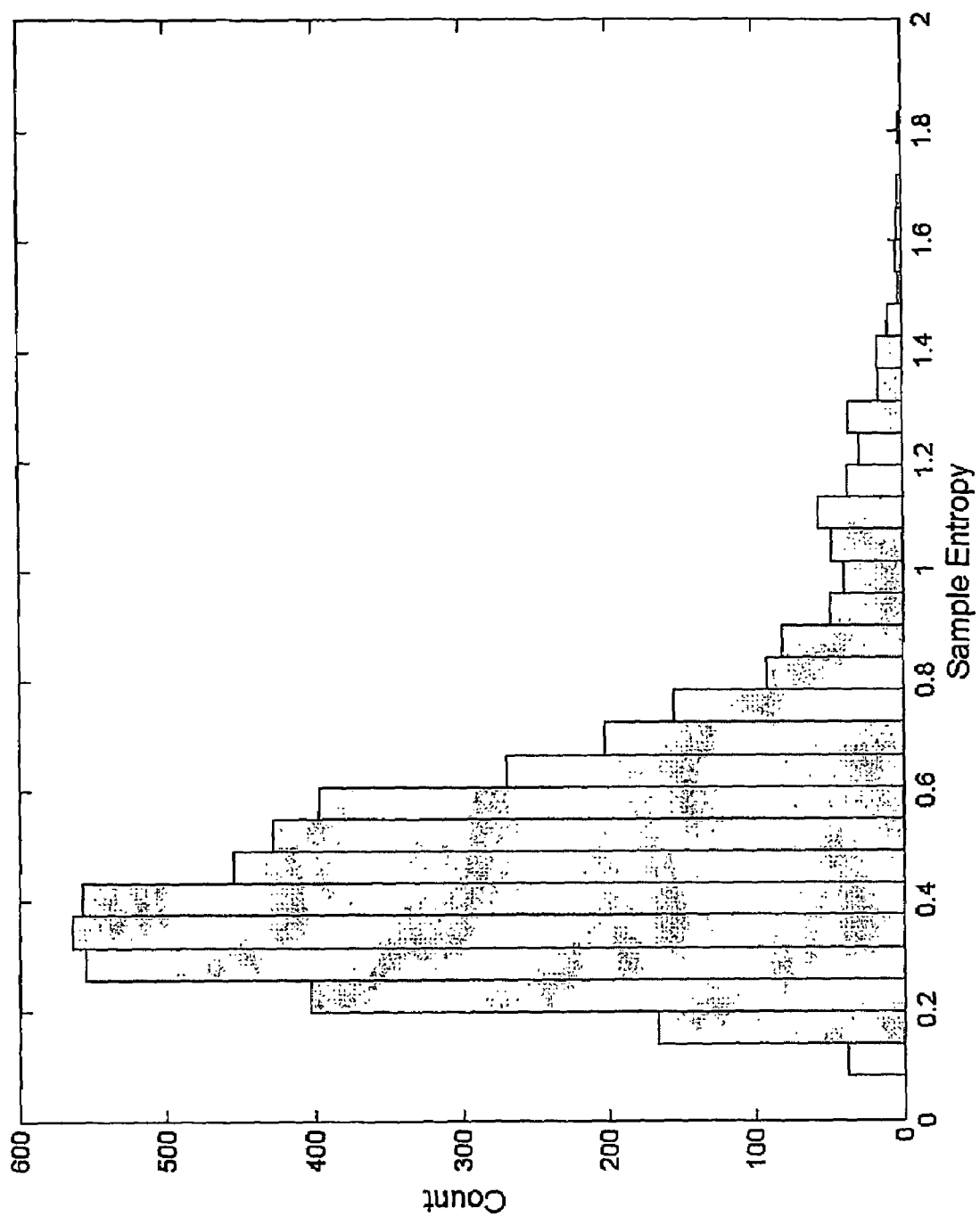

FIG. 9 is a graphical representation showing the frequency histogram of Sample Entropy, which also showed a tail toward higher values.

Figure 10:
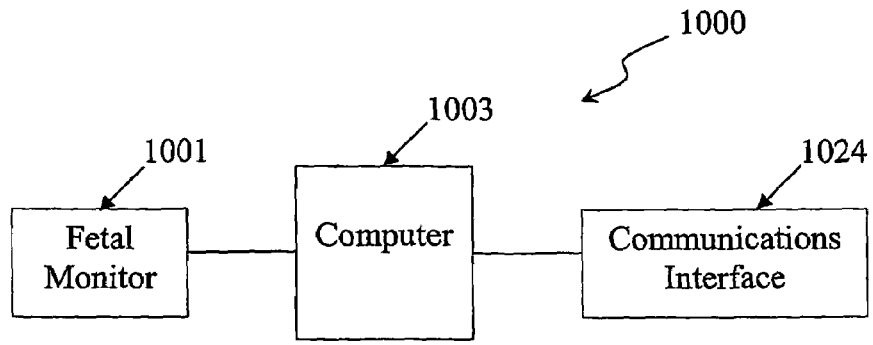

FIG. 10 is a schematic illustration of an aspect of an embodiment of the present invention.

Figure 11:
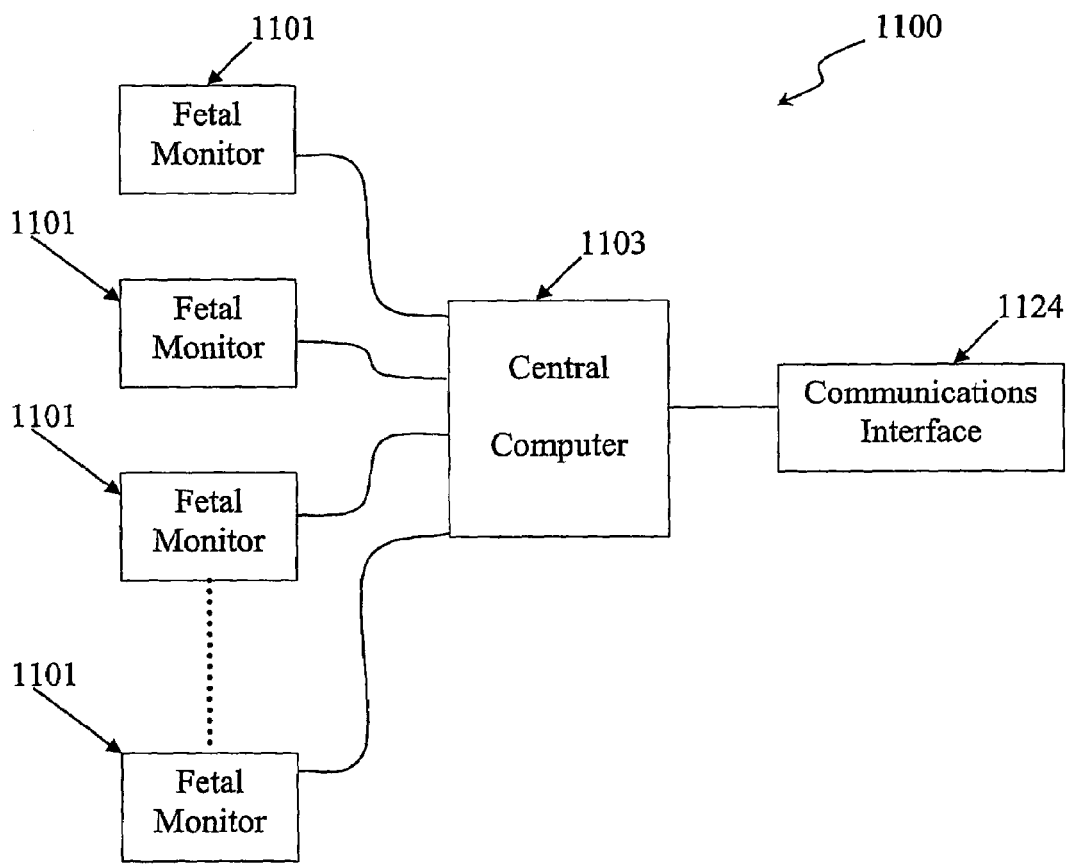

FIG. 11 is a schematic illustration of an aspect on an embodiment of the present invention.

Figure 12:
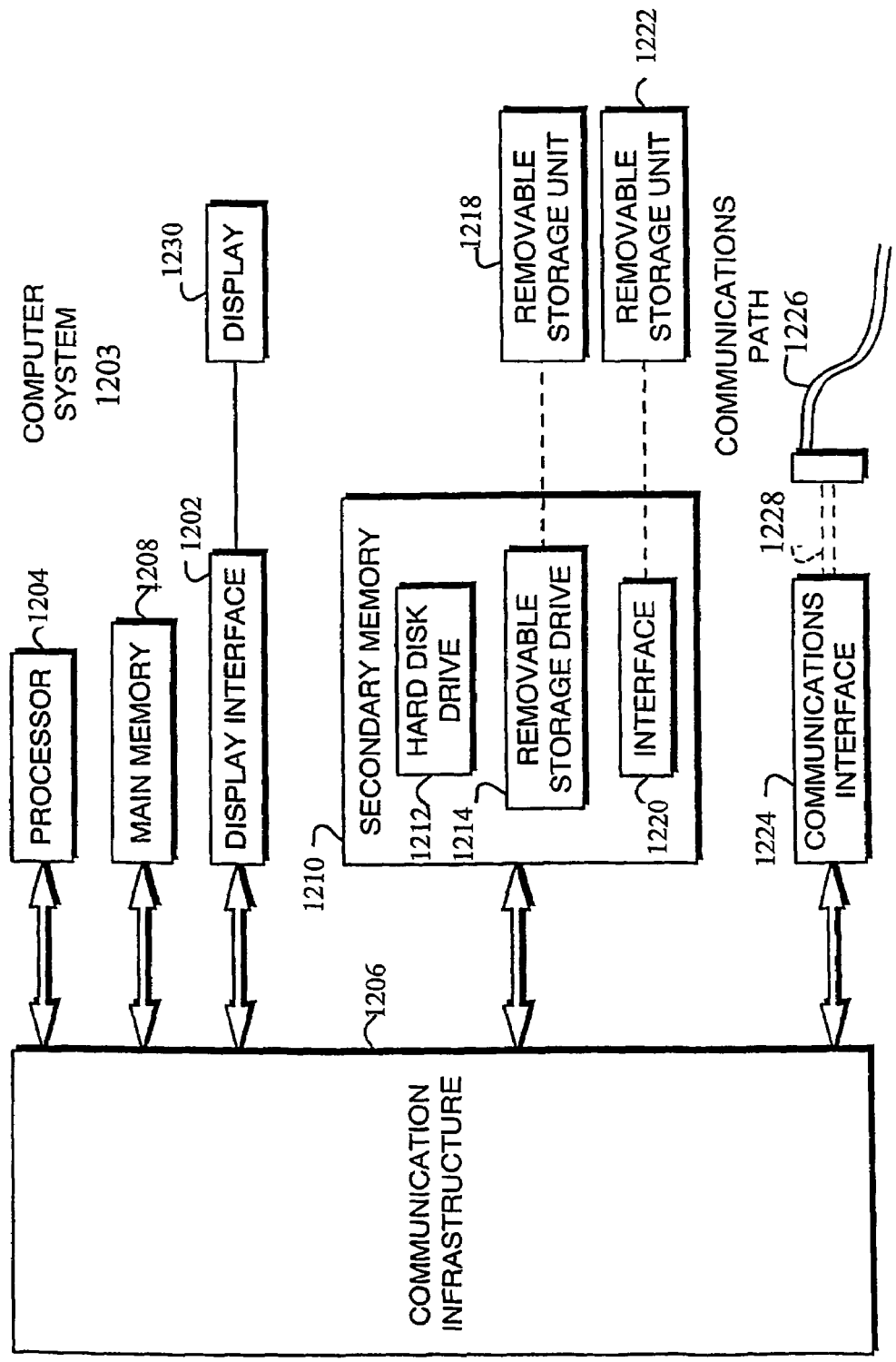

FIG. 12 is an example embodiment of an aspect of the invention as implemented in software running on a general-purpose computer.

DETAILED DESCRIPTION OF THE INVENTION

In the following, first presented is an exemplary embodiment of a fetal heart rate monitoring for practicing the methods of the present invention. Following are descriptions of preferred and alternative embodiments of the methods of the present invention, including their exemplary implementation as computer hardware, firmware, and/or software.

The present invention is a method, system, and computer program product are for, among other things, quantitative analysis of heart rate characteristics from fetal heart rate monitors that gives information about the well-being of the fetus and the risk of poor fetal outcome. The method comprises (a) continuously measuring fetal heart rate and/or cardiotocographic characteristics and (b) identifying at least one characteristic abnormality in the heart rate and/or cardiotocographic characteristics that is associated with fetal distress.

Referring to FIG. 10, FIG. 10 is a schematic illustration of an embodiment of the present invention that includes an apparatus 1000 for providing information about the well-being of the fetus and the risk of poor fetal outcome. The apparatus comprises: (a) a monitoring device 1001 that measures fetal heart rate and/or cardiotocographic characteristics and (b) computer system 1003 comprised of a microprocessor, identifying at least one characteristic abnormality in the heart rate characteristics that is associated with fetal distress. Computer system 1003 may also include a communications interface 1024. Communications interface 1024 allows software and data to be transferred between computer system 1003 and external devices or the like.

In an embodiment, the at least one characteristic is identified from a normalized set of RR intervals or heart rates, the times from one fetal heartbeat to the next. The at least one characteristic is based on the identification of one or more of the following kinds of measures 1) the second and higher moments; 2) the quantile or percentile values; 3) the sample entropy; 4) the sample asymmetry; 5) measures of stationarity based on the empirical cumulative distribution function; and 6) cross-correlation of FHR and uterine pressure tracings.

In an embodiment of the present invention, the microprocessor may perform a variety of functions comprising, but not limited thereto, calculating: 1) the second and higher moments; 2) the quantile or percentile values; 3) the sample entropy; 4) the sample asymmetry; 5) measures of stationarity based on the empirical cumulative distribution function; and 6) cross-correlation of FHR and uterine pressure tracings.

Referring to FIG. 11, FIG. 11 is a schematic illustration of an embodiment of the present invention that includes an apparatus 1100 for providing information about the well-being of the fetus and the risk of poor fetal outcome. In this embodiment additional calculation of quantitative analysis of heart rate characteristics from fetal heart rate and/or cardiotocogram can be incorporated into a stand-alone monitoring device 1001, while other tasks are performed in the central computer 1103. Consequently, the central computer 1103 can function as a central monitoring station, in which information can be shared or exchanged locally or remotely. See, for example, U.S. Pat. No. 6,192,320B1 to Margrey et al. entitled "Interactive Remote Sample Analysis System, of which is assigned to the present assignee and is hereby incorporated by reference herein in its entirety. The computer system 1103 may also include a communications interface 1124. Communications interface 1124 allows software and data to be transferred between computer system 1103 and external devices or the like.

The method and apparatus of the present invention (as discussed throughout this document) may be implemented using hardware, software or a combination thereof and may be implemented in one or more computer systems or other processing systems, or partially performed in processing systems such as personal digit assistants (PDAs). In an example embodiment, the invention was implemented in software running on a general-purpose computer 1203 as illustrated in FIG. 12. Computer system 1203 includes one or more processors, such as processor 1204. Processor 1204 is connected to a communication infrastructure 1206 (e.g., a communications bus, crossover bar, or network). Computer system 1203 includes a display interface 1202 that forwards graphics, text, and other data from the communication infrastructure 1206 (or from a frame buffer not shown) for display on the display unit 1230.

Computer system 1203 also includes a main memory 1208, preferably random access memory (RAM), and may also include a secondary memory 1210. The secondary memory 1210 may include, for example, a hard disk drive 1212 and/or a removable storage drive 1214, representing a floppy disk drive, a magnetic tape drive, an optical disk drive, etc. The removable storage drive 1214 reads from and/or writes to a removable storage unit 1218 in a well-known manner. Removable storage unit 1218, represents a floppy disk, magnetic tape, optical disk, etc. which is read by and written to by removable storage drive 1214. As will be appreciated, the removable storage unit 1218 includes a computer usable storage medium having stored therein computer software and/or data.

In alternative embodiments, secondary memory 1210 may include other means for, allowing computer programs or other instructions to be loaded into computer system 1203. Such means may include, for example, a removable storage unit 1222 and an interface 1220. Examples of such removable storage units/interfaces include a program cartridge and cartridge interface (such as that found in video game devices), a removable memory chip (such as a ROM, PROM, EPROM or EEPROM) and associated socket, and other removable storage units 1222 and interfaces 1220 which allow software and data to be transferred from the removable storage unit 1222 to computer system 1200.

Computer system 1203 may also include a communications interface 1224. Communications interface 1224 allows software and data to be transferred between computer system 1203 and external devices. Examples of communications interface 1224 may include a modem, a network interface (such as an Ethernet card), a communications port, a PCMCIA slot and card, etc. Software and data transferred via communications interface 1224 are in the form of signals 1228 which may be electronic, electromagnetic, optical or other signals capable of being received by communications interface 1224. Signals 1228 are provided to communications interface 1224 via a communications path (i.e., channel) 1226. Channel 1226 carries signals 1228 and may be implemented using wire or cable, fiber optics, a phone line, a cellular phone link, blue tooth, an IR link, an RF link and other communications channels.

In this document, the terms "computer program medium" and "computer usable medium" are used to generally refer to media such as removable storage drive 1214, a hard disk installed in hard disk drive 1212, and signals 1228. These computer program products are means for providing software to computer system 1203. The invention includes such computer program products.

Computer programs (also called computer control logic) are stored in main memory 1208 and/or secondary memory 1210. Computer programs may also be received via communications interface 1224. Such computer programs, when executed, enable computer system 1203 to perform the features of the present invention as discussed herein. In particular, the computer programs, when executed, enable processor 1204 to perform the functions of the present invention. Accordingly, such computer programs represent controllers of computer system 1203.

In an embodiment where the invention is implemented using software, the software may be stored in a computer program product and loaded into computer system 1203 using removable storage drive 1214, hard drive 1212 or communications interface 1224. The control logic (software), when executed by the processor 1204, causes the processor 1204 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in Java, but could be implemented in other program languages, such as C++, that would be appreciated by those skilled in the art.

Cross-Correlation of Fetal Heart Rate and Uterine Contractions

In an embodiment of the present invention the method, system, computer program product identifies decelerations of FHR that occur late relative to uterine contractions. A robust approach to investigating time-relationships between waveforms is cross-correlation. Conceptually, the operation is to slide one time series past the other, computing the sum of the products of the aligned terms. When similar structures of the two series are aligned, the sum will be large. Thus the expected findings of cross-correlation of the FHR and uterine pressure tracings when a deceleration is late are (1) a large and negative peak that (2) occurs after an appreciable shift of the series in time. Referring to FIGS. 1-4, FIGS. 1(A), 1(B), 2(A), 2(B), 3(A), 3(B), 4(A) and 4(B), the Y-axis is a raw fetal heart rate (HR) and uterine contraction (TOCO) data over 10 minutes. The X-axis is time scale in second multiplied by 4, since there are 4 sampling points per second.

Still referring to FIGS. 1-4, FIGS. 1(C), 2(C), 3(C), 4(C) represent how the heart rate changes relative to the uterine contraction. In these, the Y-axis is beats per minute (bpm) and the X-axis is the time by which the two traces are shifted relative to each other.

In each case, the minimum value occurs at a time lag greater than 0. This is interpreted as HR deceleration after the peak of the uterine contraction. Two values are given. The first is the time of the minimum value, and the second is its magnitude. For example, FIG. 1(C) shows an average deceleration of 3.3 beats per minute occurring 25 seconds after the peak of the contraction.

The mathematical algorithm is as follows:
(1) Normalize TOCO as mean 0 and standard deviation 1;

$$T=[TOCO-\text{mean}(TOCO)]/\text{std}(TOCO)$$

(2) Calculate the cross correlation between the normalized TOCO T and the raw HR data H by multiplying them, adding the result together and dividing by the number of points that actually contribute to the summation. The formula is:

$$C(l) = \frac{1}{N}\sum_{n=0}^{N-1} T(n)H(n=1), 1 = 0, 1, 2, \ldots N-1,$$

where C(l) is the cross correlation at lag l. When the shift makes the deceleration of HR occur at the same time as the contraction occurs, C(l) will reach a minimum value for the value of l that maximally aligns the two traces. If the contraction and the deceleration occur simultaneously, the minimum value occurs at l=0.

This is a simple and robust calculation that has advantages over inspection of the clinical recording alone. It gives quantitative, observer-independent information on the extent and timing of FHR decelerations relative to uterine contraction.

Lomb Periodogram of Fetal Heart Rate

The cross correlation calculation does not give information on reduced variability. Accordingly, the present invention calculates the variance of the fetal heart rate in several frequency bands corresponding to very low frequency (VLF), low-frequency (LF) and high-frequency (HF) bands. The preferred implementation is using the Lomb periodogram, which is insensitive to missing points (a common real world problem in fetal monitoring). The Lomb periodogram is equivalent to the least squares fitting of the data to the sinusoid: A cos(2πft)+B sin(2πft). One embodiment is to calculate the Lomb periodograms of 1-minute segment overlapping by 30 seconds.

The Lomb periodogram (See Scargle, J. D., "Studies in Astronomical Time Series Analysis: II. Statistical Aspects of Spectral Analysis of Unevenly Spaced Data," *Astrophysical Journal*, vol. 263 pp. 835-853, 1982; Home, J. H. and Baliunas, S. L., "A Prescription for Period Analysis of Unevenly Sampled Time Series," *Astrophysical Journal*, vol. 302 pp. 757-763, 1986; and Press, W. H. and Rybicki, G. B., "Fast Algorithm for Spectral Analysis of Unevenly Sampled Data," *Astrophysical Journal*, vol. 338 pp. 277-280, 1989), of which are hereby incorporated by reference herein in their entirety) of a time series with N points $|h_j, t_j: 0 \leq j \leq N-1|$ is $$P_N(f) = \frac{1}{N}\left(\frac{\left[\sum_j (h_j - \bar{h})\cos(2\pi f(t_j - \tau))\right]^2}{\sum_j \cos^2(2\pi f(t_j - \tau))} + \frac{\left[\sum_j (h_j - \bar{h})\sin(2\pi f(t_j - \tau))\right]^2}{\sum_j \sin^2(2\pi f(t_j - \tau))}\right),$$

where $\tau$ satisfies the relation $$\tan(4\pi f \tau) = \frac{\sum_j \sin(4\pi f t_j)}{\sum_j \cos(4\pi f t_j)},$$

The method integrated the very-low-frequency band (VLF, 0 to 0.03 Hz), low frequency band (LF, 0.03 to 0.15 Hz) and high frequency band (HF, 0.5 to 1 Hz). See Signorini, M. G., Magenes, G., Cerutti, S., and Arduini, D., "Linear and Nonlinear Parameters for the Analysis of Fetal Heart Rate Signal from Cardiotocographic Recordings," *IEEE Transactions on Biomedical Engineering*, vol. 50, no. 3, pp. 365-374, 2003, of which is hereby incorporated by reference.

Sample Entropy of Fetal Heart Rate

Further, the sample entropy is calculated. The pattern of reduced variability and transient deceleration leads to low value of sample entropy (SampEn). See Lake, D. E., Richman, J. S., Griffin, M. P., and Moorman, J. R., "Sample Entropy Analysis of Neonatal Heart Rate Variability," *American Journal of Physiology*, vol. 283 pp. R789-R797, 2002, of which is hereby incorporated by reference. This statistic has less bias compared to approximate entropy, especially for short data sets. See Richman, J. S. and Moorman, J. R., "Physiological Time Series Analysis Using Approximate Entropy And Sample Entropy," *American Journal of Physiology*, vol. 278 pp. H2039-H2049, 2000, of which is hereby incorporated by reference. See U.S. application Ser. No. 09/793,653 filed Feb. 27,2001, entitled "Method and Apparatus for the Early Detection of Subacute, Potentially, Catastrophic Illness," The method calculated SampEn (N=1200, m=3, r=0.1) on non-overlapping windows of 5-minute duration. Since the data were sampled at 4 Hz, m=3 has a specific meaning that the fourth point compares to the other three points in one second of time. Sample entropy (SampEn), which is a measure of the relative paterness of data series. SampEn measures complexity and regularity of clinical and experimental time series data. It is the negative logarithm of the conditional probability that two sequences of m+1 points will match within a tolerance r given that they match for the first m points.

For a time-series $x_1, x_2, \ldots, x_N$, let $x_m(i)$ denote the m points $x_i, x_{i+1}, \ldots, x_{i+m-1}$ which we call a template and can be considered a vector of length m. When all the components of the vector $x_m(j)$ are within a distance r of $x_m(i)$, there is a template match. Let $B_i$ denote the number of template matches with $x_m(i)$ and $A_i$ denote the number of template matches with $x_{m+1}(i)$. Then $p_i = A_i/B_i$ is an estimate of the conditional probability that the point $x_{j+m}$ is within r of $x_{i+m-1}$ given that $x_m(j)$ matches $x_m(i)$. We define sample entropy or SampEn as:

$$SampEn(m, r, N) = -\log\left(\sum_{i=1}^{N-m} A_i \bigg/ \sum_{i=1}^{N-m} B_i\right)$$

i.e., the negative (natural) logarithm of the conditional probability of a match of length m+1 given a match of length m throughout the data set, not template-by-template.

Sample Asymmetry of Fetal Heart Rate

Moreover, it should be appreciated that an embodiment includes calculating the sample asymmetry of the fetal heart rate. See U.S. application Ser. No. 09/793,653 filed Feb. 27, 2001, entitled "Method and Apparatus for the Early Detection of Subacute, Potentially, Catastrophic Illness," One characteristic of abnormal fetal heart rate is a marked asymmetry of the distribution of heart rates accompanied by an occurrence of large deviations caused by decelerations. We construct a quadratic function that will be used for weighting the deviation of each heart rate value from the median value. The two branches of this parabola quantify deviations towards increase (we call this R2) and decrease (R1) of an inter-beat interval with respect to the median. We compute $r_1(x_i) = r(x_i)$ if $x_i < m$; 0 otherwise, and $r_2(x_i) = r(x_i)$ if $x_i > m$; 0 otherwise for each inter-beat reading $x_i$. $R_1$ and $R_2$ are computed as:

$$R_1 = \frac{1}{n}\sum_{i=1}^{n} r_1(x_i)^2 \quad \text{and} \quad R_2 = \frac{1}{n}\sum_{i=1}^{n} r_2(x_i)^2$$

respectively. $R_1$ and $R_2$ are non-negative quantities that increase when the number and/or the magnitude of large deviations from the median increases. Intuitively, a distribution of inter-beat intervals that is skewed to the right will result in $R_2 > R_1$. We define sample asymmetry as $R_2/R_1$.

Moments and Percentiles

Moments are standard descriptors of the location and dispersion of a distribution. The rth sample moment $\mu_n$ of a data set $x_1, x_2, \ldots, x_n$ is:

$$\mu_n = \frac{1}{n}\sum_{i=1}^{n} x_i^r.$$

The first moment is the mean. If the mean is 0, the moments are called central moments. The second central moment is the variance ($\sigma^2$), a familiar measure of the dispersion. The third central moment is the skewness, which measures the deviation of the distribution from symmetry. A distribution with a tail toward large values has positive skewness. The fourth central moment about the mean is the kurtosis, which measures "peakedness" of the distribution. A distribution that is flatter or more peaked than the normal distribution has greater and lesser kurtosis, respectively. The characteristic abnormality of fetal distress is positive skewness.

The percentile (or quantile) of a distribution of values is a number $x_p$ such that a proportion p of the population values are less than or equal to $x_p$. For example, the 10th percentile of a variable (we call this p10) is a value such that 10% of the values of the variable fall below that value, The characteristic abnormality early in the course of neonatal sepsis is values of p10 that are nearer 0.

The present invention method calculates the moments and percentiles of the fetal heart rate in overlapping moving windows of 30 seconds, calculated every 15 seconds, and report the median value of the most recent 20 values.

An embodiment of the present invention comprises a method, system and computer program product that includes, for example, mathematical algorithms that perform calculations on novel measures of heart rate characteristics to yield a number that is proportional to the degree of fetal distress and/or risk of poor fetal outcome. An advantage of the present invention over the current art is that, among other things, there is not a quantitative analysis available that is optimized for detection of the characteristic heart rate abnormality of reduced baseline variability and transient heart rate decelerations. The present invention algorithm can be utilized as part of commercially available fetal heart rate monitoring systems, and could use heart rate data already processed and presented for qualitative analysis by the health care provider.

In an embodiment or combination of embodiments, the process of the present invention would comprise:

1) obtaining simultaneous recordings of fetal RR intervals or heart rates and uterine pressure;

2) implementing the cross-correlation analysis, and note the values of the extent of the decelerations (negative peak value, and area) and delay relative to the uterine contraction;

3) normalize the fetal RR interval values by subtracting the mean and dividing by the standard deviation;

4) on sets of predetermined length, calculate: the second, third and fourth higher moments; the percentiles of interest (say the 10th, 50th and 90th); the sample entropy; sample asymmetry, and measures of stationarity based on analysis of empirical cumulative distribution functions; and 5) use these measures in multivariable statistical models such as, but not limited thereto, regression models, nearest-neighbor models, neural networks, or other as desired.

It should be appreciated that the present invention can be implemented as software algorithms in existing FHR and/or CTG monitors and systems.

The patient populations and clinical settings where the present invention can be used include, for example but not limited thereto, all antepartum and intrapartum surveillance.

In an embodiment of the present invention, FHR data and uterine contraction data were collected continuously according to the *Agilent Technologies' Digital Interface Protocol Specification Programmer's Guide* from serial ports of the Corometrics 120 Series monitors connected to PCs in the 10 delivery rooms at the University of Virginia Hospital. The data were sampled 4 times per second and labeled with time stamps. The method used data from external and internal monitoring. FHR data ranged from 0 to 300 bpm with resolution of 0.25 bpm, and uterine contraction data (TOCO) was measured with 8-bit resolution. The method analyzed records that: (1) were 2 hours or longer; (2) contained 50 or more contractions; (3) were more than 90% complete for the entire course of labor.

Additionally, an aspect included the quantification of FHR decelerations and, accelerations associated with uterine contraction using cross-correlation analysis. Regarding missing data, the FHR and CTG data often had missing points due to signal artifact. The method neglected FHR values of 0 or those that differed by more than 30 bpm from their neighbors. Seventy-nine percent of 1-minute FHR and CTG records were greater than 95% complete. Regarding, the uterine contraction detection, the uterine contraction data points of greater than 0.65 standard deviations above the mean of 3-minute windows were selected as candidates for the peaks of contractions. The starting and ending points of each contraction were determined using amplitude and duration criteria. Contractions of very low amplitude and those shorter than 30 seconds were ignored.

Additionally, a cross correlation calculation was implemented. The method quantified the association between each uterine contraction and the corresponding FHR with a modified cross-correlation with following formula:

$$C(l) = \sum_{n=1}^{N} [FHR(n+l) - \text{baseline}(FHR)] TOCO(n),$$

$$l = -\text{max}lag, -\text{max}lag + 1, \ldots 0, 1, 2, \ldots \text{max}lag.$$

wherein C(l) is the cross correlation of unit bpm at lag 1; N is number of points of the TOCO studied. TOCO(n) is uterine contraction index linearly scaled to area 1 and has arbitrary units. FHR(n) is nth raw FHR datum in unit of bpm. Baseline FHR was estimated by a moving average procedure on 5-minute windows. It is important to note that an individual contraction might be accompanied by both an early acceleration and a later deceleration. See Freeman, R. K., "Problems with Intrapartum Fetal Heart Rate Monitoring Interpretation and Patient Management," *Obstet. Gynecol.*, vol. 100, no. 4, pp. 813-826, Oct.2002. If uterine contraction and deceleration of HR occur simultaneously, Cmin is expected to occur at l=0. The method defined a deceleration to be present when there was at least one local minimum less than 0. The method defined an acceleration to be present when there was at least one local maximum greater than 0. The values of 1 at the minimum and maximum value of C(l) were interpreted as the time lag of deceleration and acceleration relative to the time of the uterine contraction. This analysis yielded the extent and time lag of FHR changes associated with uterine contraction, and allowed quantification of FHR decelerations and accelerations. Since the late deceleration the method was interested in usually occurs within 60 seconds after contraction, the method set the maximum lag=90 seconds.

For this exemplary embodiment of the invention, 69 cases were analyzed. The $25^{th}$, $50^{th}$, and $75^{th}$ percentiles for gestational age, birth weight, 1-minute Apgar scores and 5-minute Apgar scores were 38/39/40 weeks, 2924/3373/3655 g, 7/8/9 and 9/9/9, respectively. The route of delivery of Cesarean, operative vaginal and spontaneous vaginal delivery were 7, 9, and 53 out of 69 cases, respectively. The number of uterine contractions detected using our algorithm is 201+/−119. In a sample of 210 detected contractions from 11 hours of recordings from 3 randomly selected patients, an expert obstetrician found a false-positive rate of 4% and a false-negative rate of 10%.

As an example of the analysis, we refer to FIG. 5, FIG. 5(A) shows a 6-minute recording of FHR, and FIG. 5(B) shows a uterine contraction. There is normal FHR variability. For figure FIG. 5(C) there is shown the cross-correlation analysis for a clinically normal record. During the contraction, there is a small deceleration that was judged to the clinically not significant.

FIG. 6 shows recording from another patient. There is reduced FHR variability, and a large late deceleration that was interpreted clinically as showing fetal distress. For both of FIGS. 5(C) and 6(C) there is shown the cross-correlation analysis. For the normal record as reflected by FIG. 5, there is a deceleration of magnitude 11.5 bpm occurring at a delay of 39.3 seconds; whereas for the abnormal record as reflected by FIG. 6(C), there is a deceleration of much larger magnitude, 69.7 bpm, occurring at a delay of 55.3 seconds. The magnitude calculated by cross-correlation are smaller than expected from inspection of the record. In FIG. 6(C), the magnitude appeared to be about 80 bpm deceleration. The reduction was due to the averaging property of the cross-correlation, and was expected to be approximately the same for all decelerations. The panels are centered at 0 as the middle point (not necessary the TOCO peak; lag l=0) of the uterine contraction, while the negative x-value represents an event in advance of the peak of the uterine contraction.

The analysis of Lomb periodogram confirmed that the variability of the FHR was reduced in FIG. 6. The median values for 1-minute segments for bands of power VLF, LF and HF were 2.3, 1.0, and 0.2 ($29^{th}$, $14^{th}$ and $71^{st}$ percentiles of all the recorded data), compared with 15.2, 11.4, and 0.95 ($70^{th}$, $77^{th}$, and $91^{st}$ percentiles) in FIG. 5. The spikes of FHR in minutes −3 to −1 in FIG. 6 were detected as artifact and treated as missing data.

Finally, the SampEn of the abnormal record was lower than that of the normal record, 0.17, compared to 0.21.

From this example, it can be appreciated that the cross-correlation analysis is likely to contain information about FHR decelerations during uterine contraction that the Lomb periodogram analysis is likely to contain information about FHR variability, and that sample entropy analysis is likely to contain information about the presence of deceleration in the presence of reduced variability in fetal HR records.

FIG. 7 shows the frequency histograms of the deceleration, acceleration and related measures. As illustrated by FIGS. 7(A) and 7(B), the amplitudes of the decelerations and accelerations have an approximately log normal distribution. As illustrated by FIG. 7(C), most decelerations occurred within 30 seconds of the peak of the uterine contraction. It is plausible to neglect decelerations at longer interval because of uncertainty about their association with uterine contraction. As illustrated by FIG. 7(D), most accelerations occurred during the rising phase of the uterine contraction, up to 50 seconds before the peak. These findings are consistent with clinical experience.

Figure 2A:
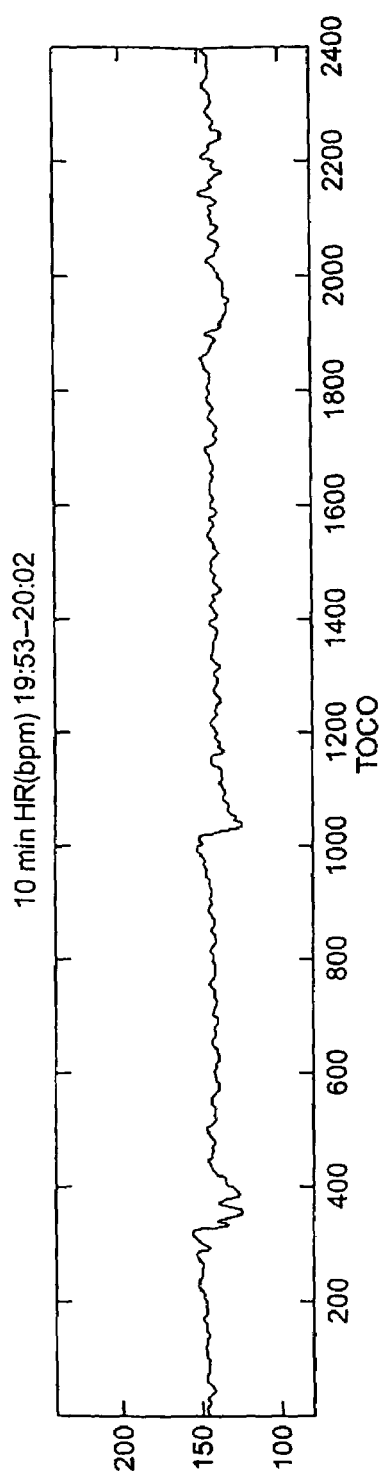
FIGS. 2(A)-(C) graphically illustrates a ten minute record subsequent to time period of FIG. 1 representing a) FHR b) uterine contraction and c) cross-correlation representing the change in FHR relative to the uterine contraction, respectively.
Figure 2B:
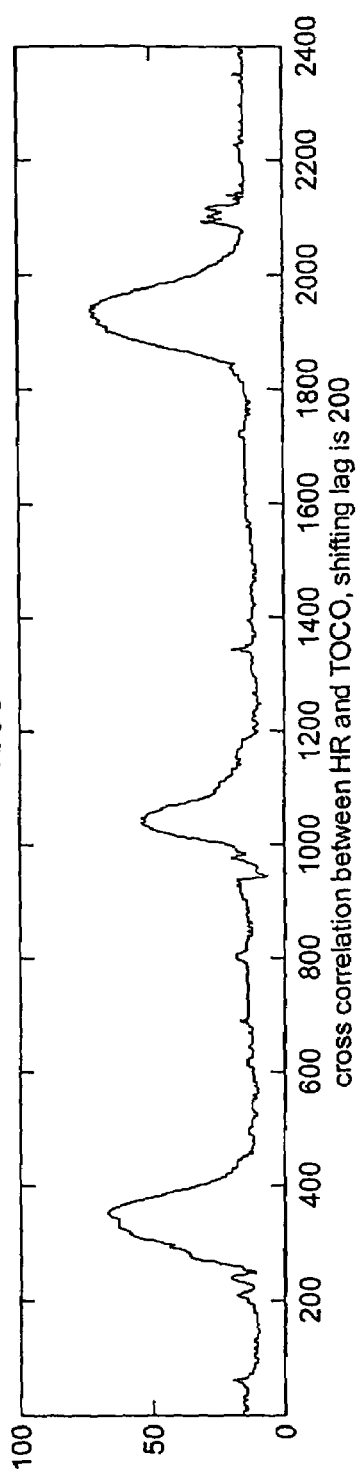
Figure 2C:
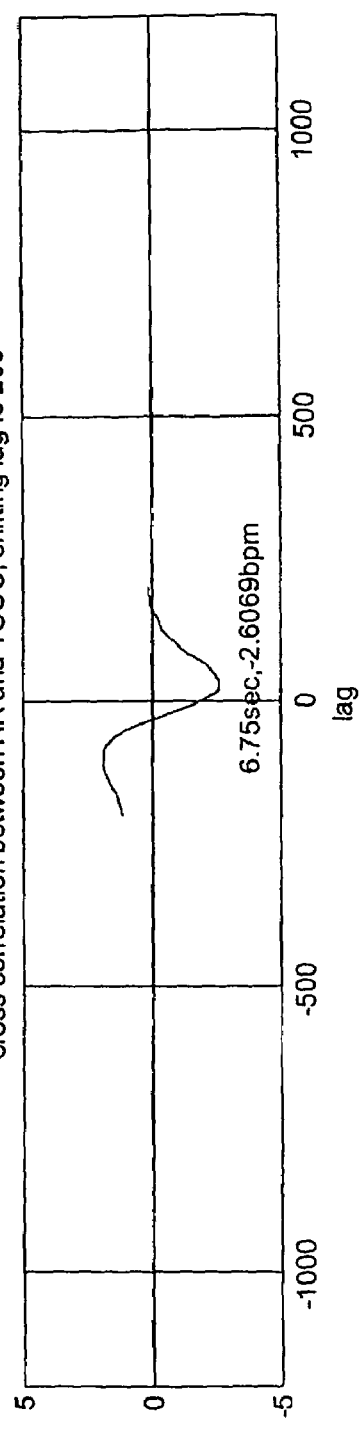
Figure 3A:
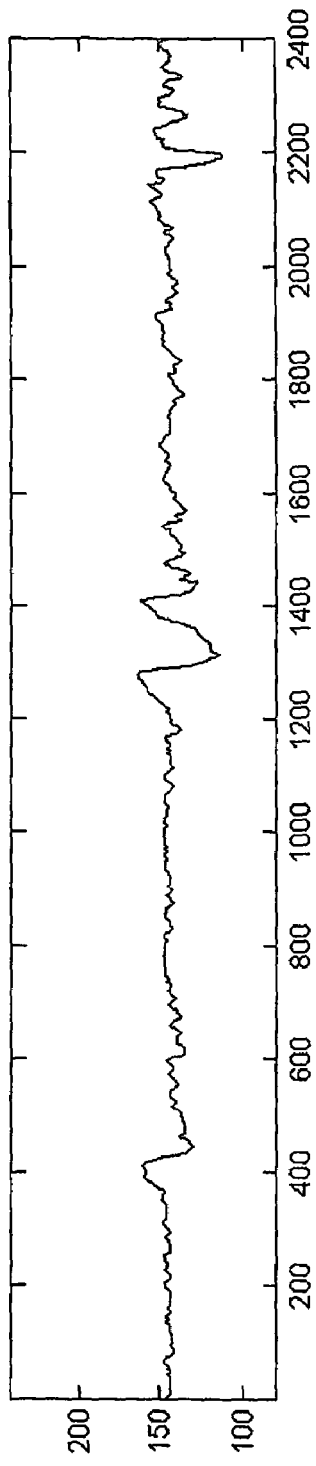
FIGS. 3(A)-(C) graphically illustrates a ten minute record subsequent to time period of FIG. 2 representing a) FHR b) uterine contraction and c) cross-correlation representing the change in FHR relative to the uterine contraction, respectively.
Figure 3B:
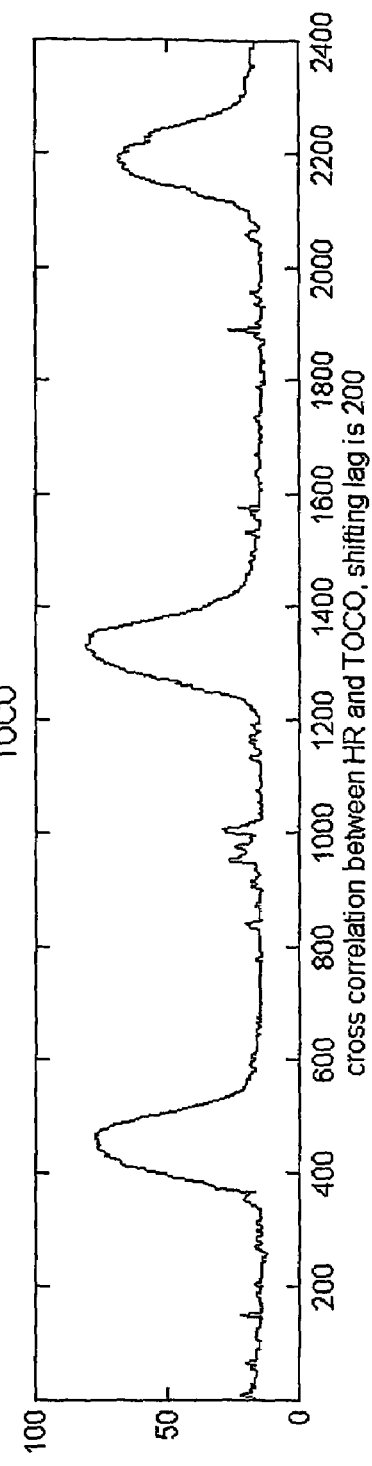
Figure 3C:
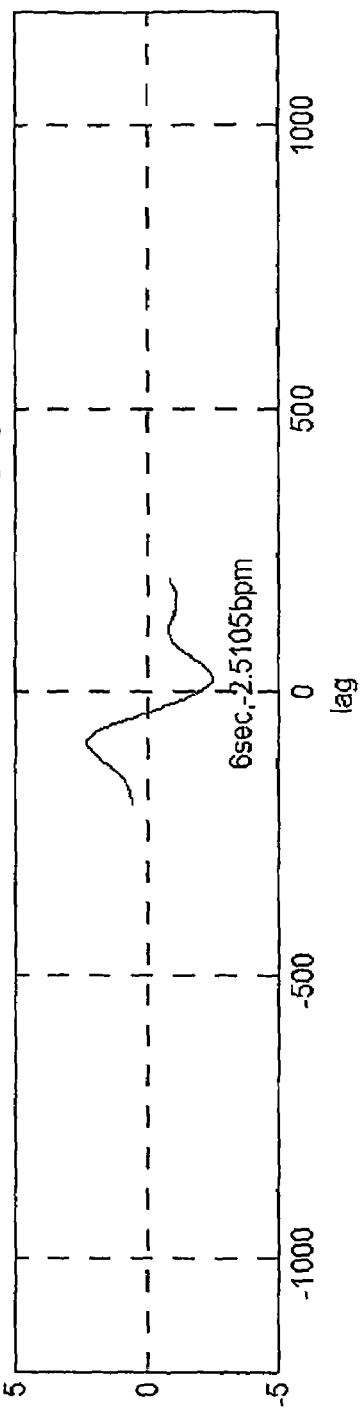
Figure 4A:
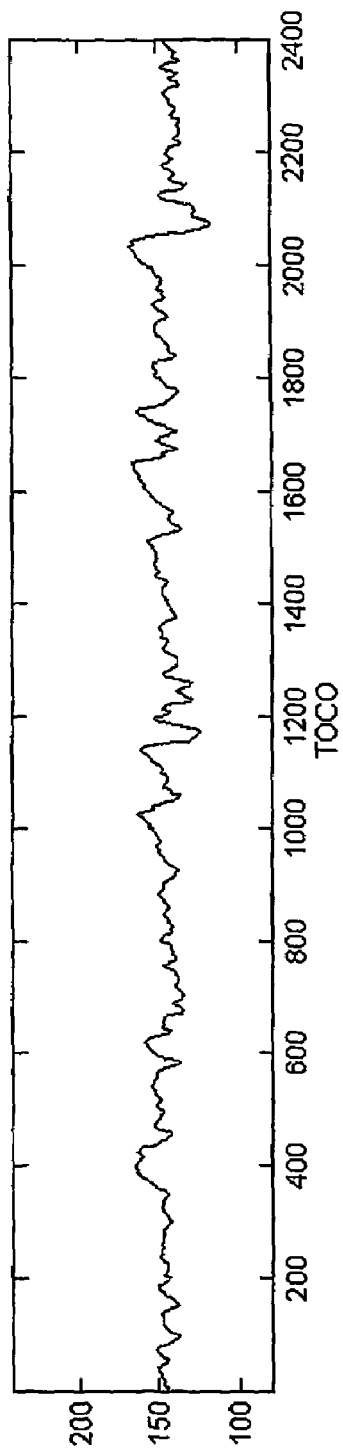
FIGS. 4(A)-(C) graphically illustrates a ten minute record subsequent to time period of FIG. 3 representing a) FHR b)
Figure 4B:
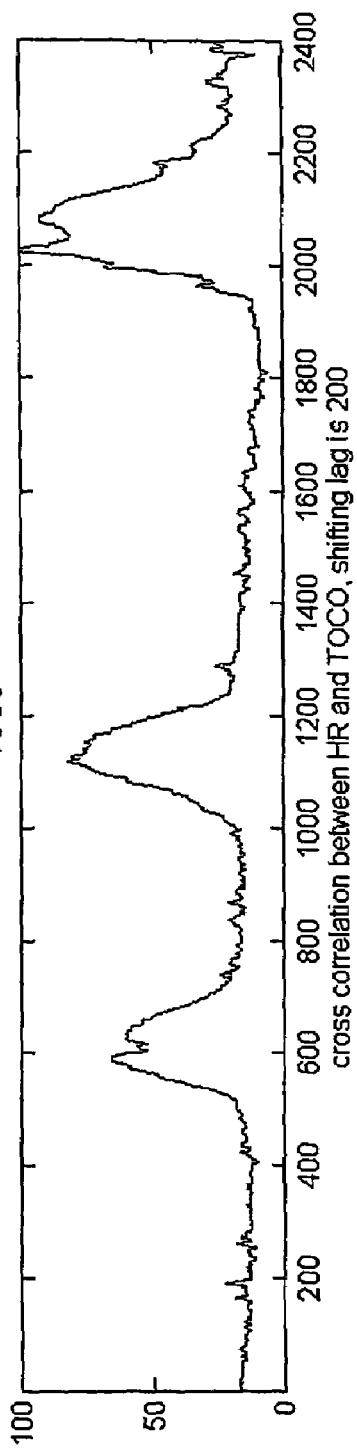
Figure 4C:
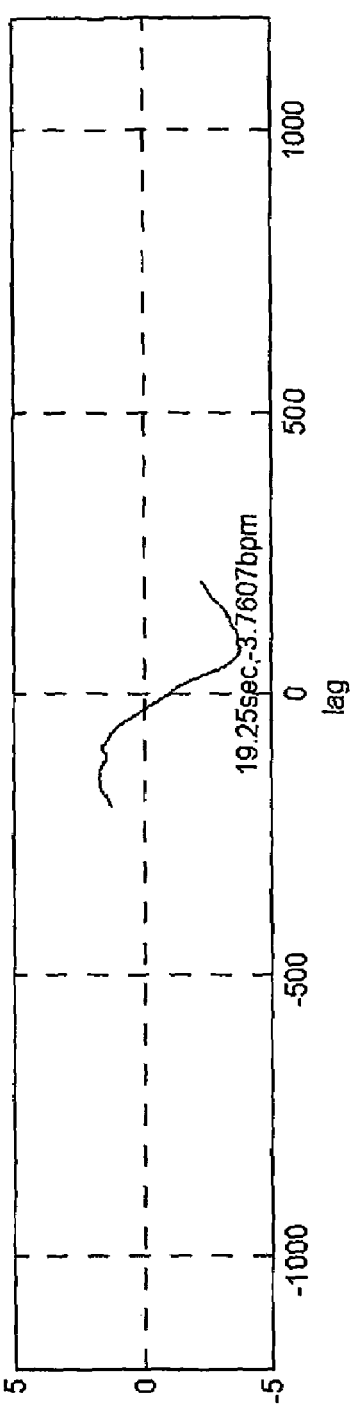
Figure 7A:
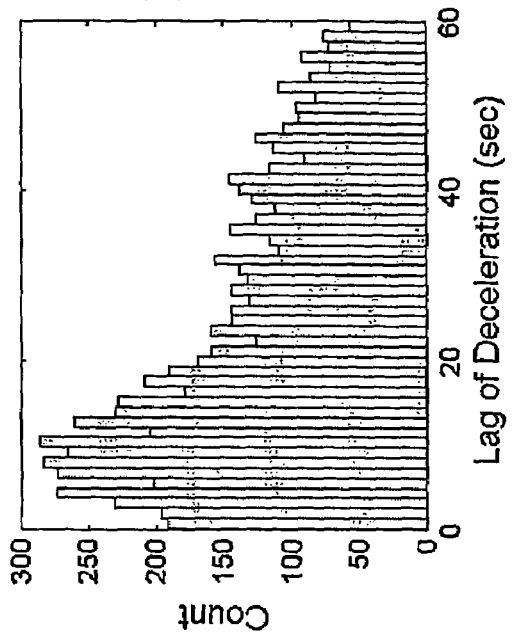
Figure 7B:
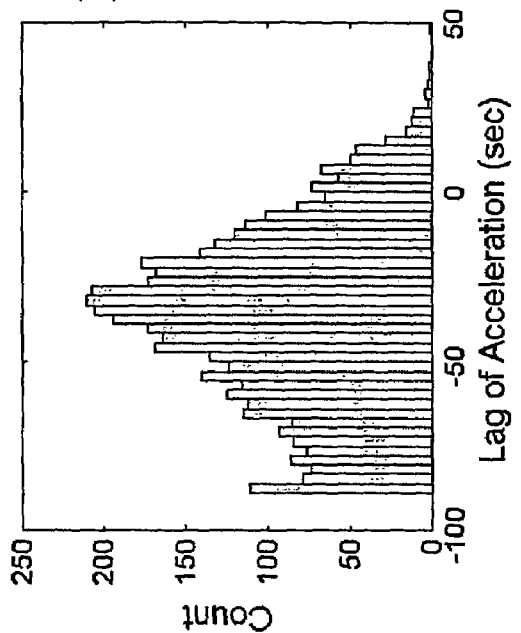
Figure 7C:
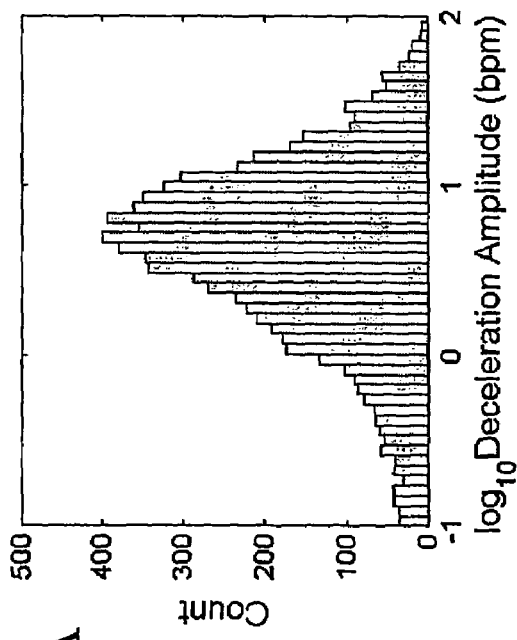
Figure 7D:
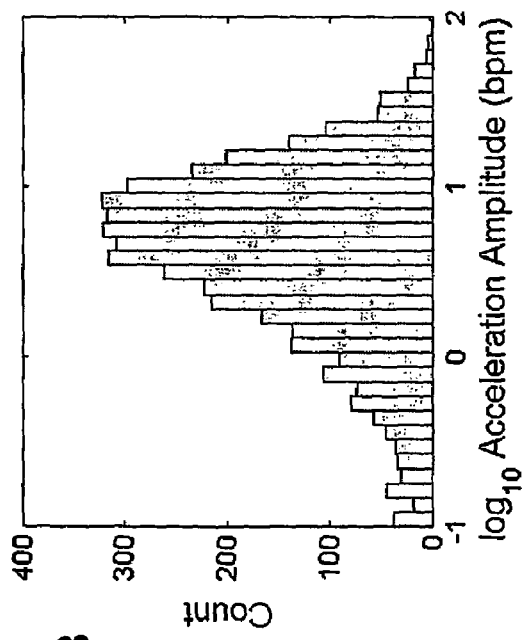
Figure 8A:
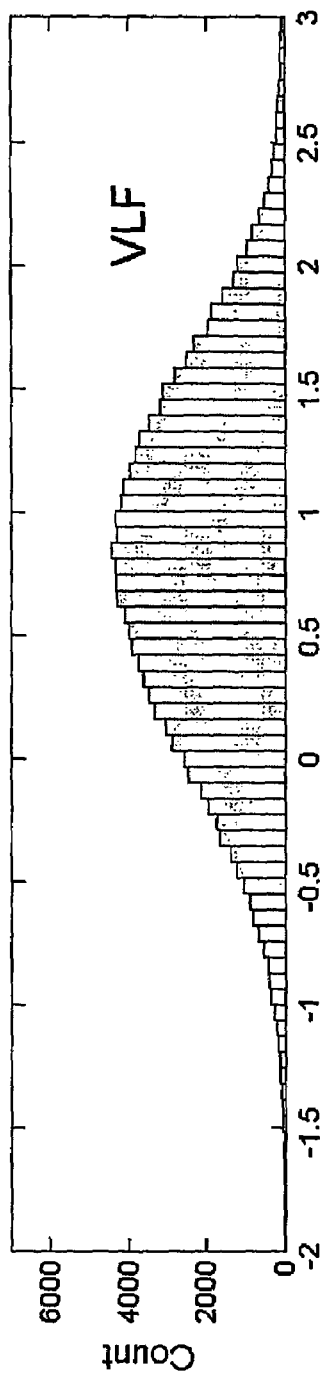
Figure 8B:
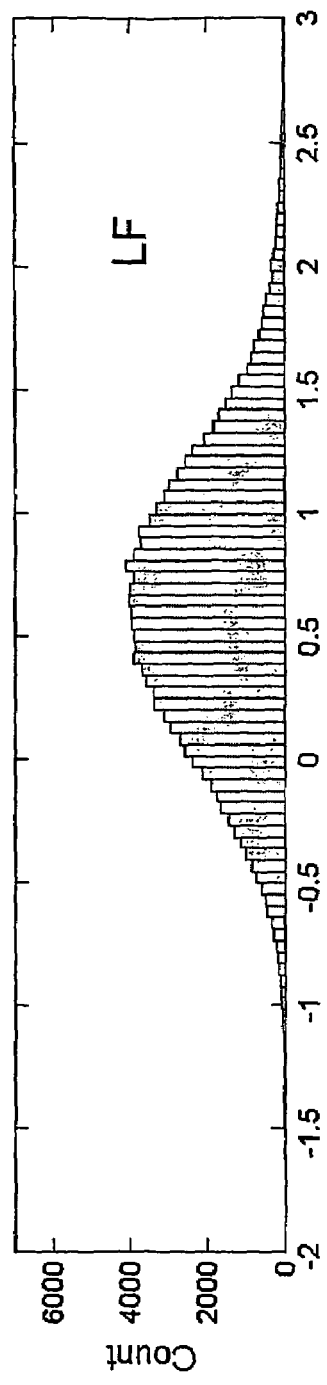
Figure 8C:
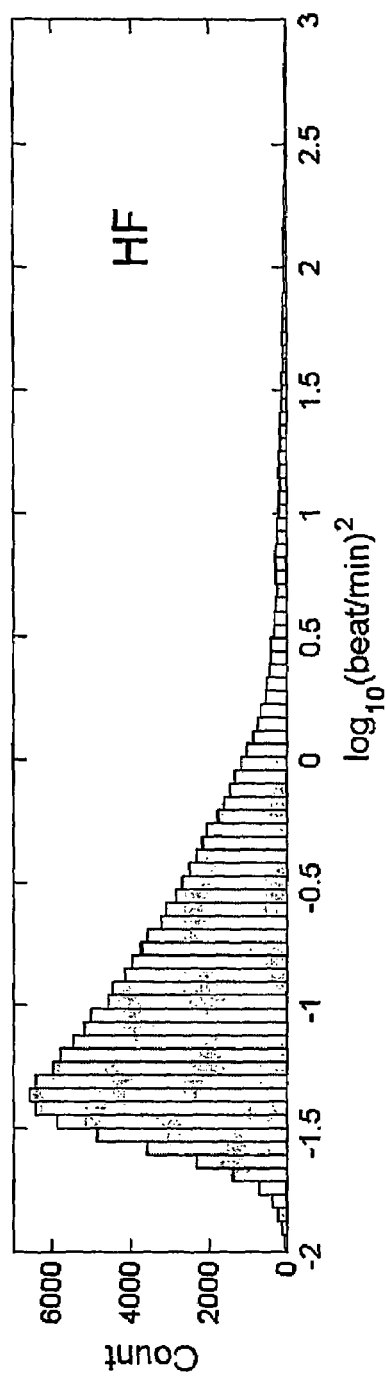

FIG. 8 shows the frequency histograms of the band-specific variances from the Lomb periodogram analysis. VLF (FIG. 8(A)) and LF (FIG. 8(B)) powers were approximately log normal, while the histogram of HF (FIG. 8(C)) power showed a long tail toward higher values. Similar to findings prior to labor, values of HF powers were lower than VLF or LF powers. See Signorini, M. G., Magenes, G., Cerutti, S., and Arduini, D., "Linear and Nonlinear Parameters for the Analysis of Fetal Heart Rate Signal from Cardiotocographic Recordings," *IEEE Transactions on Biomedical Engineering*, vol. 50, no. 3, pp. 365-374.

FIG. 9 shows the frequency histogram of Sample Entropy, which also showed a tail toward higher values. A systematic evaluation awaits optimal selection of m and r. See Lake, D. E., Richman, J. S., Griffin, M. P., and Moorman, J. R., "*Sample Entropy Analysis of Neonatal Heart Rate Variability*," American Journal of Physiology, vol. 283 pp. R789-R797, 2002.

While physicians may have recognized the importance of FHR patterns, especially the changes associated with uterine contractions, the qualitative implementation of these conventional principles has not led to large improvements in maternal or fetal outcomes. The present invention method and system have, among other things, implemented time series analysis of FHR and/or CTG patterns during active labor to begin to test the hypothesis that quantitative FHR and/or CTG monitoring may lead to improved patient care. In this clinical data set, there were no cases of emergent operative intervention because of fetal distress. A finding pursuant to the present invention is that histograms of observed values mirror clinical experience.

While the clinical data often contained signal artifact or missing data points, importantly, each of the analytical techniques described are insensitive to missing points. For instance, in the cross-correlation, products where one of the terms was missing were omitted from the averaging. The Lomb periodogram is designed for analysis of unevenly sampled points. For detection of reduced variability and transient decelerations in HR records, missing points have little effect on sample entropy analysis, a finding that the present invention method have interpreted to mean that this abnormality is not due to a change in order.

In summary, the present invention quantitative approach to FHR and/or CTG monitoring may lead to a useful clinical strategy in the care of patients in labor.

The following U.S. Patents are hereby incorporated by reference herein in their entirety:

U.S. Pat. No. 6,254,537 B1 to Nguyen, entitled "Fetal Outcome Predictor and Monitoring System;"

U.S. Pat. No. 5,957,855 to Oriol et al., entitled "Fetal Data Processing System and Method Employing a Time-Frequency Representation of Fetal Heart Rate;"

U.S. Pat. No. 5,596,993 to Oriol et al., entitled "Fetal Data Processing System and Method;" and U.S. Pat. No. 5,442,940 to Secker et al., entitled "Apparatus and Method for Evaluating the Fetal Condition."

An advantage associated with at least an aspect of an embodiment of the present invention as it pertains to the mother, among other things, includes, but not limited thereto, the following: allows earlier diagnosis of intra-amniotic infection; categorizes fetuses as "healthy" versus "at risk" more accurately and therefore lessen maternal complications of cesarean delivery, provides operative vaginal delivery and trauma (from intervention); decreases hospital expenditures and length of stay; reduces family burden of caring for chronically ill/debilitated neonates and children by recognizing and acting on information from this monitoring in timely manner; and provides more judicious diagnosis of intra-amniotic infection and use of antibiotics, leading to less development of antibiotic resistance and adverse effects of antibiotic administration.

An advantage associated with at least an aspect of an embodiment of the present invention as it pertains to the fetus, among other things, includes, but not limited thereto, the following: reduces mortality; reduces NICU admissions; improves outcome measures associated with fetal distress and sepsis/intra-amniotic infection; improves immediate outcome measures of asphyxia such as blood gases and acid-base state, Apgar scores, neurologic examination, presence of seizures; improve organ function (e.g. heart, circulation, respiration, kidneys, coagulation system, liver); improves long-term outcome measures such as cerebral palsy, intelligence quotient, other organ dysfunction; and provides more judicious diagnosis of intra-amniotic infection and use of antibiotics, leading to less development of antibiotic resistance and adverse effects of antibiotic administration.

The patient populations and clinical settings where the present invention can be used include, for example but not limited thereto, all antepartum and intrapartum surveillance in which evaluation of fetal well-being is a goal.

Accordingly, the patient population and clinical setting associated with at least an aspect of an embodiment of the present invention as it pertains to the antepartum period, among other things, includes, but not limited thereto, the following: pre-term labor; premature or prolonged rupture of membranes; hypertensive and/or vascular disease of the mother, such as pregnancy-induced hypertension, pre-eclampsia, eclampsia; multiple gestations; hemorrhage; intra-uterine growth restriction; suspected or impending chorioamnionitis; infectious disease of the fetus; Rh incompatibility and other isoinmunization disorders; fetal anemia; during fetal surgery; during amniocentesis or chorionic villus sampling; and maternal diabetes.

Accordingly, the patient population and clinical setting associated with at least an aspect of an embodiment of the present invention as it pertains to the intrapartum period, among other things, includes, but not limited thereto, the following: 1st and 2nd stages of active labor; fetal intolerance of labor; placental complications, such as placenta previa and placental abruption; prolapsed umbilical cord; fetal-pelvic disproportion; malpresentation; infectious disease of the fetus; hemorrhage; suspected or impending chorioamnionitis; and suspected or impending perinatal compromise.

In addition, the present invention computer program product, method and apparatus can be used to assess the degree of fetal CNS and physiological maturation. The present invention computer program product, method, and apparatus can be applied to FUR and/or CTG recordings made invasively or non-invasively, and in the inpatient and outpatient setting, regardless of whether or not there is active labor.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension, time period, or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. A computer method for evaluating fetal well-being and predicting fetal outcome, said method comprising:
   a) obtaining simultaneous recordings of fetal heart rate and maternal uterine pressure;
   b) calculating one or more parameters:
      i. cross-correlation of the fetal heart rate and the uterine pressure,
      ii. Lomb periodogram of the fetal heart rate,
      iv. sample entropy of the fetal heart rate,
      v. sample asymmetry of the fetal heart rate, and
      vi. one or more of:
         second, third and fourth higher moments, and
         percentiles of interest of the fetal heart rate; and
   c) determining heart rate characteristic of fetal distress by comparing one of said parameters to a predetermined threshold or mathematical model.

2. The method of claim 1, wherein the calculating step is carried out using a multivariable statistical analysis.

3. The method of claim 2, wherein said multivariable statistical analysis is selected from at least one of but not limited to regression models, nearest-neighbor models, and neural networks, and any combination thereof.

4. The method of claim 1, wherein the implementation of percentiles of interest include 10th, 50th and/or 90th.

5. The method of claim 1, wherein the cross-correlation analysis comprises amplitude and timing relative to uterine contractions of accelerations and decelerations of the fetal heart rate.

6. The method of claim 1, wherein the cross-correlation analysis comprises:
   normalizing uterine contraction data, referenced as TOCO, as mean of 0 and standard deviation of 1 according to the formula:

$T = [TOCO - \text{mean}(TOCO)]/\text{std}(TOCO),$ calculating the cross correlation between T and the raw HR data H according the formula:

$$C(l) = \frac{1}{N} \sum_{n=0}^{N-1} T(n) H(n=l), \, l = 0, 1, 2, \ldots N - 1,$$

wherein C(l) is the cross correlation at lag l.

7. The method of claim 6, wherein C(l) will reach a minimum value for the value of l that maximally aligns the two traces; and
   if the contraction and the deceleration occur simultaneously, the minimum value occurs at l=0.

8. The method of claim 1, wherein the Lomb periodogram is the variance of the fetal heart rate that is attributed to very low frequency (VLF), low-frequency (LF), and high-frequency (HF) oscillations.

9. The method of claim 1, wherein the Lomb periodogram of a time series with N points $|h_j, t_j: 0=j=N-1|$ is calculated according to the formula:

$$P_N(f) = \frac{1}{N} \left( \frac{\left[ \sum_j (h_j - \overline{h}) \cos(2\pi f(t_j - \tau)) \right]^2}{\sum_j \cos^2(2\pi f(t_j - \tau))} + \frac{\left[ \sum_j (h_j - \overline{h}) \sin(2\pi f(t_j - \tau)) \right]^2}{\sum_j \sin^2(2\pi f(t_j - \tau))} \right),$$

where τ satisfies the relation $$\tan(4\pi f \tau) = \frac{\sum_j \sin(4\pi f t_j)}{\sum_j \cos(4\pi f t_j)}.$$

10. The method of claim 1, wherein the sample entropy of a time series $x_1, x_2, \ldots, x_N$, wherein $x_m(i)$ denote the m points $x_i, x_{i+1}, \ldots, x_{i+m-1}$ which defines a template and can be considered a vector of length m;
   wherein when all the components of the vector $x_m(j)$ are within a distance r of $x_m(i)$, there is a template match;
   wherein $B_i$ denotes the number of template matches with $x_m(i)$;

wherein $A_i$ denotes the number of template matches with $x_{m+1}(i)$;

wherein $p_i=A_i/B_i$ is an estimate of the conditional probability that the point $x_{j+m}$ is within r of $x_{i+m-1}$ given that $x_m(j)$ matches $x_m(i)$; and wherein sample entropy is defined according to the formula:

$$SampEn(m, r, N) = -\log\left(\sum_{i=1}^{N-m} A_i \Big/ \sum_{i=1}^{N-m} B_i\right).$$

11. The method of claim 1, wherein the sample asymmetry comprises:

quantifying deviations of an inter-beat interval with respect to the median towards an increase referred to as R2 and towards a decrease referred to as R1;

compute $r_1(x_i)=r(x_i)$ if $x_i<m$; 0 otherwise, and $r_2(x_i)=r(x_i)$ if $x_i>m$; 0 otherwise for each inter-beat reading $x_i$;

wherein $R_1$ and $R_2$ are computed as:

$$R_1 = \frac{1}{n}\sum_{i=1}^{n} r_1(x_i)^2 \quad \text{and} \quad R_2 = \frac{1}{n}\sum_{i=1}^{n} r_2(x_i)^2, \text{ and}$$

wherein the sample asymmetry is determined by the formula $R_2/R_1$.

12. The method of claim 1, wherein the second and/or higher moments are calculated with the data set $x_1, x_2, \ldots, x_N$, according to the formula:

$$\mu_n = \frac{1}{n}\sum_{i=1}^{n} x_i^r.$$

13. The method of claim 1, wherein at least one of the following is provided:

earlier diagnosis of intra-amniotic infection; categorization of fetus health or fetus risk;

and diagnosis of intra-amniotic, or any combination thereof.

14. The method of claim 1, wherein the method is applied during antepartum period or intrapartum period or both antepartum period and intrapartum period.

15. The apparatus of claim 1, wherein the second and/or higher moments are calculated with the data set $x_1, x_2, \ldots, x_N$, according to the formula:

$$\mu_n = \frac{1}{n}\sum_{i=1}^{n} x_i^r.$$

16. An apparatus for evaluating fetal well-being and predicting fetal outcome, said apparatus comprising:

a) a monitoring device, which monitors the fetal heart rate and maternal uterine pressure;

b) a microprocessor, said microprocessor performing the steps of:

calculating one or more parameters:

i. cross-correlation of the fetal heart rate and the uterine pressure, ii. Lomb periodogram of the fetal heart rate, iii. sample entropy of the fetal heart rate, iv. sample asymmetry of the fetal heart rate, and v. one or more of:

second, third and fourth higher moments, and percentiles of interest of the fetal heart rate; and determining heart rate characteristics of fetal distress by comparing one of said parameters to a predetermined threshold or mathematical model.

17. The apparatus of claim 16, wherein the calculating step is carried out using a multivariable statistical analysis.

18. The apparatus of claim 17, wherein said multivariable statistical analysis is selected from at least one of but not limited to regression models, nearest-neighbor models, and neural networks, and any combination thereof.

19. The apparatus of claim 16, wherein the implementation of percentiles of interest include 10th, 50th and/or 90th.

20. The apparatus of claim 16, wherein the cross-correlation analysis comprises amplitude and timing relative to uterine contractions of accelerations and decelerations of the fetal heart rate.

21. The apparatus of claim 16, wherein the cross-correlation analysis comprises:

normalizing uterine contraction data, referenced as TOCO, as mean of 0 and standard deviation of 1 according to the formula:

$T=[TOCO-\text{mean}(TOCO)]/\text{std}(TOCO),$ calculating the cross correlation between T and the raw HR data H according the formula:

$$C(l) = \frac{1}{N}\sum_{n=0}^{N-1} T(n)H(n=1), 1 = 0, 1, 2, \ldots N-1,$$

wherein C(l) is the cross correlation at lag l.

22. The apparatus of claim 21, wherein C(l) will reach a minimum value for the value of l that maximally aligns the two traces; and if the contraction and the deceleration occur simultaneously, the minimum value occurs at l=0.

23. The apparatus of claim 16, wherein the Lomb periodogram is the variance of the fetal heart rate that is attributed to very low frequency (VLF), low-frequency (LF), and high-frequency (HF) oscillations.

24. The apparatus of claim 16, wherein the Lomb periodogram of a time series with N points $|h_j, t_j: 0=j=N-1|$ is calculated according to the formula:

$$P_N(f) = \frac{1}{N}\left(\frac{\left[\sum_j (h_j - \bar{h})\cos(2\pi f(t_j - \tau))\right]^2}{\sum_j \cos^2(2\pi f(t_j - \tau))} + \frac{\left[\sum_j (h_j - \bar{h})\sin(2\pi f(t_j - \tau))\right]^2}{\sum_j \sin^2(2\pi f(t_j - \tau))}\right),$$

where τ satisfies the relation $$\tan(4\pi f \tau) = \frac{\sum_j \sin(4\pi f t_j)}{\sum_j \cos(4\pi f t_j)}.$$

25. The apparatus of claim 16, wherein the sample entropy of a time series $x_1, x_2, \ldots, x_N$, wherein $x_m(i)$ denote the m points $x_i, x_{i+1}, \ldots, x_{i+m-1}$ which defines a template and can be considered a vector of length m;
   wherein when all the components of the vector $x_m(j)$ are within a distance r of $x_m(i)$, there is a template match;
   wherein $B_i$ denotes the number of template matches with $x_m(i)$;
   wherein $A_i$ denotes the number of template matches with $x_{m+1}(i)$;
   wherein $p_i = A_i/B_i$ is an estimate of the conditional probability that the point $x_{j+m}$ is within r of $x_{i+m-1}$ given that $x_m(j)$ matches $x_m(i)$; and
   wherein sample entropy is defined according to the formula:

$$SampEn(m, r, N) = -\log\left(\sum_{i=1}^{N-m} A_i \Big/ \sum_{i=1}^{N-m} B_i\right).$$

26. The apparatus of claim 16, wherein the sample asymmetry comprises:
   quantifying deviations of an inter-beat interval with respect to the median towards an increase referred to as R2 and towards a decrease referred to as R1;
   compute $r_1(x_i) = r(x_i)$ if $x_i < m$; 0 otherwise, and $r_2(x_i) = r(x_i)$ if $x_i > m$; 0 otherwise for each inter-beat reading $x_i$;

wherein $R_1$ and $R_2$ are computed as:

$$R_1 = \frac{1}{n}\sum_{i=1}^{n} r_1(x_i)^2 \quad \text{and} \quad R_2 = \frac{1}{n}\sum_{i=1}^{n} r_2(x_i)^2, \text{ and}$$

wherein the sample asymmetry is determined by the formula $R_2/R_1$.

27. The apparatus of claim 16, wherein at least one of the following is provided: earlier diagnosis of intra-amniotic infection; categorization of fetus health or fetus risk; and diagnosis of intra-amniotic, or any combination thereof.

28. The apparatus of claim 16, wherein the method is applied during antepartum period or intrapartum period or both antepartum period and intrapartum period.

29. A computer program product comprising computer usable medium having computer logic for enabling at lease one processor in a computer system to evaluate fetal well-being and predicting fetal outcome based on a monitoring device, which monitors the fetal heart rate and maternal uterine pressure, said computer logic comprising:
   calculating one or more parameters:
      i. cross-correlation of the fetal heart rate and the uterine pressure,
      ii. Lomb periodogram of the fetal heart rate,
      iii. sample entropy of the fetal heart rate,
      iv. sample asymmetry of the fetal heart rate, and
      v. one or more of:
         second, third and fourth higher moments; and
         percentiles of interest of the fetal heart rate; and
   determining heart rate characteristic of fetal distress by comparing one of said parameters to a predetermined threshold or mathematical model.

* * * * *